United States Patent
Huebner et al.

(10) Patent No.: US 7,537,603 B2
(45) Date of Patent: May 26, 2009

(54) BONE FUSION SYSTEM

(75) Inventors: Randall J. Huebner, Beaverton, OR (US); David G. Jensen, Troutdale, OR (US); Herbert Respess, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 449 days.

(21) Appl. No.: 10/625,503

(22) Filed: Jul. 22, 2003

(65) Prior Publication Data

US 2004/0127901 A1 Jul. 1, 2004

Related U.S. Application Data

(60) Provisional application No. 60/484,262, filed on Jun. 30, 2003, provisional application No. 60/398,075, filed on Jul. 22, 2002.

(51) Int. Cl.
*A61B 17/88* (2006.01)
(52) U.S. Cl. ...................................... 606/281
(58) Field of Classification Search ............. 606/69–71, 606/280, 281, 282, 283–297; 623/21.11–21.17, 623/17.11–17.16
See application file for complete search history.

(56) References Cited

U.S. PATENT DOCUMENTS

| | | | |
|---|---|---|---|
| 820,503 A | 5/1906 | Krengel et al. |
| 869,697 A | 10/1907 | Eilhauer et al. |
| 1,105,105 A | 7/1914 | Sherman |
| 1,345,425 A | 7/1920 | Wells |
| 1,789,060 A | 1/1931 | Weisenbach |
| 1,889,239 A | 11/1932 | Crowley |
| 2,406,832 A | 9/1946 | Hardinge |
| 2,443,363 A | 6/1948 | Townsend et al. |
| 2,489,870 A | 11/1949 | Dzus |
| 2,500,370 A | 3/1950 | McKibbin |
| 2,526,959 A | 10/1950 | Lorenzo |
| 2,494,229 A | 11/1950 | Collison |
| 2,583,896 A | 1/1952 | Siebrandt |
| 2,580,821 A | 11/1952 | Nicola |
| 2,737,835 A | 3/1956 | Herz |
| 3,025,853 A | 3/1962 | Mason |
| 3,072,423 A | 1/1963 | Charlton |
| 3,171,518 A | 3/1965 | Bergmann |
| 3,244,170 A | 4/1966 | McElvenny |
| 3,346,894 A | 10/1967 | Lemelson |
| 3,386,437 A | 6/1968 | Treace |
| 3,488,779 A | 1/1970 | Christensen |
| 3,489,143 A | 1/1970 | Halloran |

(Continued)

FOREIGN PATENT DOCUMENTS

AU 89750/91 2/1992

(Continued)

OTHER PUBLICATIONS

McBride S.M.O. Stainless Steel Bone Plates brochure, DePuy, Inc., 1943.

(Continued)

*Primary Examiner*—Eduardo C Robert
*Assistant Examiner*—Michael J Araj
(74) *Attorney, Agent, or Firm*—Kolisch Hartwell, PC

(57) ABSTRACT

Systems, including apparatus, methods, and kits, for fusing two or more bones with a bone plate.

78 Claims, 4 Drawing Sheets

U.S. PATENT DOCUMENTS

| | | | |
|---|---|---|---|
| 3,593,709 A | 7/1971 | Halloran |
| 3,604,414 A | 9/1971 | Borges |
| 3,716,050 A | 2/1973 | Johnston |
| 3,741,205 A | 6/1973 | Markolf et al. |
| 3,842,825 A | 10/1974 | Wagner |
| 3,866,458 A | 2/1975 | Wagner |
| 3,900,025 A | 8/1975 | Barnes, Jr. |
| 3,901,064 A | 8/1975 | Jacobson |
| 3,939,497 A | 2/1976 | Heimke et al. |
| 3,965,720 A | 6/1976 | Goodwin et al. |
| 4,119,092 A | 10/1978 | Gil |
| 4,187,840 A | 2/1980 | Watanabe |
| 4,187,841 A | 2/1980 | Knutson |
| 4,201,215 A | 5/1980 | Crossett et al. |
| 4,364,382 A | 12/1982 | Mennen |
| 4,388,921 A | 6/1983 | Sutter et al. |
| 4,408,601 A | 10/1983 | Wenk |
| RE31,628 E | 7/1984 | Allgower et al. |
| 4,457,307 A | 7/1984 | Stillwell |
| 4,484,570 A | 11/1984 | Sutter et al. |
| 4,488,543 A | 12/1984 | Tornier |
| 4,493,317 A | 1/1985 | Klaue |
| 4,506,681 A | 3/1985 | Mundell |
| 4,513,744 A | 4/1985 | Klaue |
| 4,565,192 A | 1/1986 | Shapiro |
| 4,565,193 A | 1/1986 | Streli |
| 4,573,458 A | 3/1986 | Lower |
| 4,651,724 A | 3/1987 | Berentey et al. |
| 4,683,878 A | 8/1987 | Carter |
| 4,703,751 A | 11/1987 | Pohl |
| 4,718,413 A | 1/1988 | Johnson |
| 4,730,608 A | 3/1988 | Schlein |
| 4,736,737 A | 4/1988 | Fargie et al. |
| 4,743,261 A | 5/1988 | Epinette |
| 4,750,481 A | 6/1988 | Reese |
| 4,757,810 A | 7/1988 | Reese |
| 4,759,350 A | 7/1988 | Dunn et al. |
| 4,760,843 A | 8/1988 | Fischer et al. |
| 4,794,918 A | 1/1989 | Wolter |
| 4,800,874 A | 1/1989 | David et al. |
| 4,823,780 A | 4/1989 | Odensten et al. |
| 4,867,144 A | 9/1989 | Karas et al. |
| 4,892,093 A | 1/1990 | Zarnowski et al. |
| 4,893,619 A | 1/1990 | Dale et al. |
| 4,903,691 A | 2/1990 | Heinl |
| 4,905,679 A | 3/1990 | Morgan |
| 4,923,471 A | 5/1990 | Morgan |
| 4,926,847 A | 5/1990 | Luckman |
| 4,943,292 A | 7/1990 | Foux |
| 4,955,886 A | 9/1990 | Pawluk |
| 4,957,497 A | 9/1990 | Hoogland et al. |
| 4,963,153 A | 10/1990 | Noesberger et al. |
| 4,964,403 A | 10/1990 | Karas et al. |
| 4,966,599 A | 10/1990 | Pollock |
| 4,973,332 A | 11/1990 | Kummer |
| 4,988,350 A | 1/1991 | Herzberg |
| 5,002,544 A | 3/1991 | Klaue et al. |
| 5,006,120 A | 4/1991 | Carter |
| 5,013,315 A | 5/1991 | Barrows |
| 5,015,248 A | 5/1991 | Burstein et al. |
| 5,021,056 A | 6/1991 | Hofmann et al. |
| 5,041,113 A | 8/1991 | Biedermann et al. |
| 5,042,983 A | 8/1991 | Rayhack |
| 5,049,149 A | 9/1991 | Schmidt |
| 5,053,036 A | 10/1991 | Perren et al. |
| 5,085,660 A | 2/1992 | Lin |
| 5,113,685 A | 5/1992 | Asher et al. |
| 5,129,899 A | 7/1992 | Small et al. |
| 5,133,718 A | 7/1992 | Mao |
| 5,139,497 A | 8/1992 | Tilghman et al. |
| 5,147,361 A | 9/1992 | Ojima et al. |
| 5,151,103 A | 9/1992 | Tepic et al. |
| 5,161,404 A | 11/1992 | Hayes |
| 5,176,685 A | 1/1993 | Rayhack |
| 5,190,544 A | 3/1993 | Chapman et al. |
| 5,190,545 A | 3/1993 | Corsi et al. |
| 5,197,966 A | 3/1993 | Sommerkamp |
| 5,201,737 A | 4/1993 | Leibinger et al. |
| 5,234,431 A | 8/1993 | Keller |
| 5,254,119 A | 10/1993 | Schreiber |
| 5,269,784 A | 12/1993 | Mast |
| 5,290,288 A | 3/1994 | Vignaud et al. |
| 5,304,180 A | 4/1994 | Slocum |
| 5,314,485 A * | 5/1994 | Judet .................. 623/21.13 |
| 5,314,490 A | 5/1994 | Wagner et al. |
| 5,364,398 A | 11/1994 | Chapman et al. |
| 5,364,399 A | 11/1994 | Lowery et al. |
| 5,380,327 A | 1/1995 | Eggers et al. |
| 5,413,577 A | 5/1995 | Pollock |
| 5,413,579 A | 5/1995 | Du Toit |
| 5,423,826 A | 6/1995 | Coates et al. |
| 5,443,516 A | 8/1995 | Albrektsson et al. |
| 5,468,242 A | 11/1995 | Reisberg |
| 5,474,553 A | 12/1995 | Baumgart |
| 5,487,741 A | 1/1996 | Maruyama et al. |
| 5,487,743 A | 1/1996 | Laurain et al. |
| 5,522,902 A | 6/1996 | Yuan et al. |
| 5,527,311 A | 6/1996 | Procter et al. |
| 5,531,745 A | 7/1996 | Ray |
| 5,534,027 A | 7/1996 | Hodorek |
| 5,545,228 A | 8/1996 | Kambin |
| 5,564,302 A | 10/1996 | Watrous |
| 5,578,036 A | 11/1996 | Stone et al. |
| 5,586,985 A | 12/1996 | Putnam et al. |
| 5,591,166 A | 1/1997 | Bernhardt et al. |
| 5,601,553 A | 2/1997 | Trebing et al. |
| 5,607,426 A | 3/1997 | Ralph et al. |
| 5,643,261 A | 7/1997 | Schafer et al. |
| 5,643,265 A | 7/1997 | Errico et al. |
| 5,647,872 A | 7/1997 | Gilbert et al. |
| 5,658,283 A | 8/1997 | Huebner |
| 5,662,655 A | 9/1997 | Laboureau et al. |
| 5,665,088 A | 9/1997 | Gil et al. |
| 5,665,089 A | 9/1997 | Dall et al. |
| 5,674,222 A | 10/1997 | Berger et al. |
| 5,676,667 A | 10/1997 | Hausman |
| 5,681,313 A | 10/1997 | Diez |
| 5,702,396 A | 12/1997 | Hoenig et al. |
| 5,707,372 A | 1/1998 | Errico et al. |
| 5,707,373 A | 1/1998 | Sevrain et al. |
| 5,709,682 A | 1/1998 | Medoff |
| 5,709,686 A | 1/1998 | Talos et al. |
| 5,718,704 A | 2/1998 | Medoff |
| 5,718,705 A | 2/1998 | Sammarco |
| 5,720,502 A | 2/1998 | Cain |
| 5,722,976 A | 3/1998 | Brown |
| 5,722,978 A | 3/1998 | Jenkins, Jr. |
| 5,730,743 A | 3/1998 | Kirsch et al. |
| 5,733,287 A | 3/1998 | Tepic et al. |
| 5,735,853 A | 4/1998 | Olerud |
| 5,741,258 A | 4/1998 | Klaue et al. |
| 5,741,259 A | 4/1998 | Chan |
| 5,749,872 A | 5/1998 | Kyle et al. |
| 5,749,873 A | 5/1998 | Fairley |
| 5,752,958 A | 5/1998 | Wellisz |
| 5,772,662 A | 6/1998 | Chapman et al. |
| 5,807,396 A | 9/1998 | Raveh |
| 5,810,823 A | 9/1998 | Klaue et al. |
| 5,810,824 A | 9/1998 | Chan |
| 5,853,413 A | 12/1998 | Carter et al. |
| D404,128 S | 1/1999 | Huebner |
| 5,855,580 A | 1/1999 | Kreidler et al. |
| 5,871,548 A | 2/1999 | Sanders et al. |
| 5,879,389 A | 3/1999 | Koshino |

| Patent | Type | Date | Inventor |
|---|---|---|---|
| 5,902,304 | A | 5/1999 | Walker et al. |
| 5,904,683 | A | 5/1999 | Pohndorf et al. |
| 5,916,216 | A | 6/1999 | DeSatnick et al. |
| 5,919,195 | A | 7/1999 | Wilson et al. |
| 5,928,234 | A | 7/1999 | Manspeizer |
| 5,931,839 | A | 8/1999 | Medoff |
| 5,938,664 | A | 8/1999 | Winquist et al. |
| 5,941,878 | A | 8/1999 | Medoff |
| 5,951,557 | A | 9/1999 | Luter |
| 5,954,722 | A | 9/1999 | Bono |
| 5,964,763 | A | 10/1999 | Incavo et al. |
| 5,968,046 | A | 10/1999 | Castleman |
| 5,968,047 | A | 10/1999 | Reed |
| 5,973,223 | A | 10/1999 | Tellman et al. |
| 6,001,099 | A | 12/1999 | Huebner |
| 6,004,323 | A | 12/1999 | Park et al. |
| 6,004,353 | A | 12/1999 | Masini |
| 6,007,535 | A | 12/1999 | Rayhack et al. |
| 6,022,350 | A | 2/2000 | Ganem |
| 6,027,504 | A | 2/2000 | McGuire |
| 6,053,915 | A | 4/2000 | Bruchmann |
| 6,077,266 | A | 6/2000 | Medoff |
| 6,077,271 | A | 6/2000 | Huebner et al. |
| 6,093,188 | A | 7/2000 | Murray |
| 6,096,040 | A | 8/2000 | Esser |
| 6,113,603 | A | 9/2000 | Medoff |
| 6,117,160 | A | 9/2000 | Bonutti |
| 6,123,709 | A | 9/2000 | Jones |
| 6,129,728 | A | 10/2000 | Schumacher et al. |
| 6,129,730 | A | 10/2000 | Bono et al. |
| 6,139,548 | A | 10/2000 | Errico |
| 6,152,927 | A | 11/2000 | Farris et al. |
| 6,156,037 | A * | 12/2000 | LeHuec et al. ............... 606/61 |
| 6,159,213 | A | 12/2000 | Rogozinski |
| 6,179,839 | B1 | 1/2001 | Weiss et al. |
| 6,183,475 | B1 | 2/2001 | Lester et al. |
| 6,193,721 | B1 | 2/2001 | Michelson |
| 6,197,028 | B1 | 3/2001 | Ray et al. |
| 6,221,073 | B1 | 4/2001 | Weiss et al. |
| 6,224,602 | B1 | 5/2001 | Hayes |
| 6,228,087 | B1 | 5/2001 | Fenaroli et al. |
| 6,235,033 | B1 | 5/2001 | Brace et al. |
| 6,235,034 | B1 | 5/2001 | Bray |
| 6,238,396 | B1 | 5/2001 | Lombardo |
| 6,258,092 | B1 | 7/2001 | Dall |
| 6,261,291 | B1 | 7/2001 | Talaber et al. |
| 6,273,889 | B1 | 8/2001 | Richelsoph |
| 6,283,969 | B1 | 9/2001 | Grusin et al. |
| 6,290,703 | B1 | 9/2001 | Ganem |
| 6,302,883 | B1 | 10/2001 | Bono |
| 6,302,884 | B1 | 10/2001 | Wellisz et al. |
| 6,302,887 | B1 | 10/2001 | Spranza et al. |
| 6,306,136 | B1 | 10/2001 | Baccelli |
| 6,312,431 | B1 | 11/2001 | Asfora |
| 6,315,779 | B1 | 11/2001 | Morrison et al. |
| 6,322,562 | B1 | 11/2001 | Wolter |
| 6,325,803 | B1 | 12/2001 | Schumacher et al. |
| 6,331,179 | B1 | 12/2001 | Freid et al. |
| 6,336,927 | B2 | 1/2002 | Rogozinski |
| 6,338,734 | B1 | 1/2002 | Burke et al. |
| 6,342,055 | B1 | 1/2002 | Eisermann et al. |
| 6,342,075 | B1 | 1/2002 | MacArthur |
| 6,355,036 | B1 | 3/2002 | Nakajima |
| 6,355,042 | B2 | 3/2002 | Winquist |
| 6,358,250 | B1 | 3/2002 | Orbay |
| 6,364,881 | B1 | 4/2002 | Apgar et al. |
| 6,364,882 | B1 | 4/2002 | Orbay |
| 6,364,883 | B1 | 4/2002 | Santilli |
| 6,379,354 | B1 | 4/2002 | Rogozinski |
| 6,379,364 | B1 | 4/2002 | Brace et al. |
| 6,402,756 | B1 | 6/2002 | Ralph et al. |
| 6,413,259 | B1 | 7/2002 | Lyons et al. |
| 6,428,542 | B1 | 8/2002 | Michelson |
| 6,436,103 | B1 | 8/2002 | Suddaby |
| 6,440,135 | B2 | 8/2002 | Orbay et al. |
| 6,454,769 | B2 | 9/2002 | Wagner et al. |
| 6,454,770 | B1 | 9/2002 | Klaue |
| 6,458,133 | B1 | 10/2002 | Lin |
| 6,503,250 | B2 | 1/2003 | Paul |
| 6,508,819 | B1 | 1/2003 | Orbay |
| 6,514,274 | B1 | 2/2003 | Boucher et al. |
| 6,520,965 | B2 | 2/2003 | Chervitz et al. |
| 6,527,775 | B1 | 3/2003 | Warburton |
| 6,533,789 | B1 | 3/2003 | Hall, IV et al. |
| 6,547,790 | B2 | 4/2003 | Harkey et al. |
| 6,565,570 | B2 | 5/2003 | Sterett et al. |
| 6,592,578 | B2 | 7/2003 | Henniges et al. |
| 6,595,993 | B2 | 7/2003 | Donno et al. |
| 6,602,255 | B1 | 8/2003 | Campbell et al. |
| 6,623,486 | B1 | 9/2003 | Weaver et al. |
| 6,623,487 | B1 | 9/2003 | Goshert |
| 6,682,531 | B2 | 1/2004 | Winquist et al. |
| 6,682,533 | B1 | 1/2004 | Dinsdale et al. |
| 6,689,139 | B2 | 2/2004 | Horn |
| 6,695,846 | B2 | 2/2004 | Richelsoph et al. |
| 6,706,046 | B2 | 3/2004 | Orbay et al. |
| 6,712,820 | B2 | 3/2004 | Orbay |
| 6,719,759 | B2 | 4/2004 | Wagner et al. |
| 6,730,090 | B2 | 5/2004 | Orbay et al. |
| 6,730,091 | B1 | 5/2004 | Pfefferle et al. |
| 6,736,819 | B2 | 5/2004 | Tipirneni |
| 6,767,351 | B2 | 7/2004 | Orbay et al. |
| 6,793,658 | B2 | 9/2004 | LeHuec et al. |
| 6,821,278 | B2 | 11/2004 | Frigg et al. |
| 6,858,031 | B2 | 2/2005 | Morrison et al. |
| 6,866,665 | B2 | 3/2005 | Orbay |
| 6,893,444 | B2 | 5/2005 | Orbay |
| 6,955,677 | B2 | 10/2005 | Dahners |
| 2001/0011172 | A1 | 8/2001 | Orbay et al. |
| 2002/0004660 | A1 | 1/2002 | Henniges et al. |
| 2002/0032446 | A1 | 3/2002 | Orbay |
| 2002/0055741 | A1 | 5/2002 | Schlapfer et al. |
| 2002/0128654 | A1 | 9/2002 | Steger et al. |
| 2002/0143336 | A1 | 10/2002 | Hearn |
| 2002/0143338 | A1 | 10/2002 | Orbay et al. |
| 2002/0147453 | A1 | 10/2002 | Gambale |
| 2002/0151899 | A1 | 10/2002 | Bailey et al. |
| 2002/0156474 | A1 | 10/2002 | Wack et al. |
| 2002/0183752 | A1 | 12/2002 | Steiner et al. |
| 2003/0040748 | A1 | 2/2003 | Aikins et al. |
| 2003/0055429 | A1 | 3/2003 | Ip et al. |
| 2003/0105461 | A1 | 6/2003 | Putnam |
| 2003/0149434 | A1 | 8/2003 | Paul |
| 2003/0153918 | A1 | 8/2003 | Putnam et al. |
| 2003/0216813 | A1* | 11/2003 | Ball et al. ............... 623/21.12 |
| 2003/0233093 | A1 | 12/2003 | Moles et al. |
| 2004/0102775 | A1 | 5/2004 | Huebner |
| 2004/0102776 | A1 | 5/2004 | Huebner |
| 2004/0102777 | A1 | 5/2004 | Huebner |
| 2004/0102778 | A1 | 5/2004 | Huebner et al. |
| 2004/0116930 | A1 | 6/2004 | O'Driscoll et al. |
| 2004/0127903 | A1 | 7/2004 | Schlapfer et al. |
| 2004/0153073 | A1 | 8/2004 | Orbay |
| 2004/0193164 | A1 | 9/2004 | Orbay |
| 2004/0193165 | A1 | 9/2004 | Orbay |
| 2004/0220566 | A1 | 11/2004 | Bray |
| 2004/0260291 | A1 | 12/2004 | Jensen |
| 2004/0260292 | A1 | 12/2004 | Orbay et al. |
| 2004/0260293 | A1 | 12/2004 | Orbay et al. |
| 2004/0260294 | A1 | 12/2004 | Orbay et al. |
| 2004/0260295 | A1 | 12/2004 | Orbay et al. |
| 2005/0015089 | A1 | 1/2005 | Young et al. |
| 2005/0049593 | A1 | 3/2005 | Duong et al. |
| 2005/0065520 | A1 | 3/2005 | Orbay |
| 2005/0065522 | A1 | 3/2005 | Orbay |
| 2005/0065523 | A1 | 3/2005 | Orbay |

| | | | |
|---|---|---|---|
| 2005/0065524 | A1 | 3/2005 | Orbay |
| 2005/0065528 | A1 | 3/2005 | Orbay |
| 2005/0085818 | A1 | 4/2005 | Huebner |
| 2005/0085819 | A1 | 4/2005 | Ellis et al. |
| 2005/0131413 | A1 | 6/2005 | O'Driscoll et al. |
| 2005/0159747 | A1 | 7/2005 | Orbay |
| 2005/0165395 | A1 | 7/2005 | Orbay et al. |
| 2005/0165400 | A1 | 7/2005 | Fernandez |
| 2005/0171544 | A1 | 8/2005 | Falkner |
| 2005/0182405 | A1 | 8/2005 | Orbay et al. |
| 2005/0182406 | A1 | 8/2005 | Orbay et al. |
| 2005/0187551 | A1 | 8/2005 | Orbay et al. |
| 2005/0192578 | A1 | 9/2005 | Horst |
| 2005/0234458 | A1 | 10/2005 | Huebner |

FOREIGN PATENT DOCUMENTS

| | | |
|---|---|---|
| CA | 2082535 | 5/1993 |
| CH | 611 147 | 5/1979 |
| DE | 2515430 | 11/1975 |
| DE | 4201531 | 7/1993 |
| DE | 4343117 | 6/1995 |
| EP | 0 053 999 | 6/1982 |
| EP | 0 410 309 | 1/1991 |
| EP | 0415837 A2 | 3/1991 |
| EP | 0471418 A1 | 2/1992 |
| EP | 0362049 B1 | 5/1992 |
| EP | 0530585 A2 | 3/1993 |
| EP | 0867149 A1 | 9/1998 |
| EP | 1 250 892 A2 | 9/2003 |
| EP | 1 250 892 A3 | 9/2003 |
| FR | 742.618 | 3/1933 |
| FR | 2 254 298 | 7/1975 |
| FR | 2367479 | 5/1978 |
| FR | 2405705 | 5/1979 |
| FR | 2405706 | 5/1979 |
| FR | 2406429 | 5/1979 |
| FR | 2472373 | 7/1981 |
| FR | 2674118 | 9/1992 |
| GB | 2245498 | 1/1992 |
| GB | 2257913 A | 1/1993 |
| JP | 49-28687-01 | 6/1947 |
| JP | 5-237135 | 9/1993 |
| JP | 6-285080 | 10/1994 |
| JP | 7-178115 | 7/1995 |
| JP | 10-314182 | 12/1998 |
| JP | 2000-512186 A | 9/2000 |
| JP | 2001-525702 A | 12/2001 |
| SU | 610518 | 6/1978 |
| SU | 718097 | 2/1980 |
| SU | 862937 | 9/1981 |
| SU | 897233 | 1/1982 |
| SU | 1049054 | 10/1983 |
| SU | 1130332 | 12/1984 |
| SU | 1192806 | 11/1985 |
| SU | 1223901 | 4/1986 |
| SU | 1225556 | 4/1986 |
| SU | 1544406 | 2/1990 |
| SU | 1630804 | 2/1991 |
| SU | 1644932 | 4/1991 |
| SU | 1683724 | 10/1991 |
| SU | 1711859 A | 2/1992 |
| SU | 1734715 A1 | 5/1992 |
| WO | WO82/01645 | 5/1982 |
| WO | WO87/02572 | 5/1987 |
| WO | WO97/47251 | 12/1987 |
| WO | WO88/03781 | 6/1988 |
| WO | WO96/29948 | 10/1996 |
| WO | WO 98/51226 A2 | 11/1998 |
| WO | WO01/21083 A1 | 3/2001 |
| WO | WO01/62136 A3 | 8/2001 |
| WO | WO02/054992 * | 7/2002 |
| WO | WO 03/105712 A2 | 12/2003 |

OTHER PUBLICATIONS

Bone Plates brochure, Vitallium, Mar. 1948.
Dupont Distal Humeral Plates brochure, Howmedica Inc., 1990.
The Arnett-TMP* Titanium Miniplating System brochure, Techmedica, Inc., 1989.
Techmedica Bioengineers Keep Tabs on Your Needs brochure, Techmedica, Inc., 1991.
A Comparison of Unicortical and Bicortical End Screw Attachment of Fracture Fixation Plates, Beaupre et al., *Journal of Orthopaedic Trauma*, vol. 6, No. 3, pp. 294-300, 1992.
Ace 4.5/5.0 mm Titanium Cannulated Screw and Reconstruction Plate System surgical technique brochure, Ace Medical Company, 1992.
Ace 4.5/5.0 mm Titanium Cannulated Screw and Reconstruction Plate System simplified fracture fixation brochure, Ace Medical Company, 1992.
Ace Titanium 3.5/4.0 mm Screw and Plate System with the Ace 3.5 mm Universal Ribbon CT/MRI compatible fixation brochure, Ace Medical Company, 1992.
Treatment of Three- and Four-Part Fractures of the Proximal Humerus with a Modified Cloverleaf Plate, Esser, *Journal of Orthopaedic Trauma*, vol. 8, No. 1, pp. 15-22, 1994.
Ace Symmetry Titanium Upper Extremity Plates surgical technique brochure, Ace Medical Company, 1996.
The Ace Symmetry Titanium Upper Extremity Plates new product release brochure, Ace Medical Company, 1996.
Small Titanium Plates overview page, Synthes, p. 2a-33, Mar. 1997.
Congruent Distal Radius Plate System description, Acumed, Inc., Mar. 4, 1998.
Salvage of Tibial Pilon Fractures Using Fusion of the Ankle with a 90° Cannulated Blade Plate: A Preliminary Report, Morgan et al., *Foot & Ankle International*, vol. 20, No. 6, pp. 375-378, Jun. 1999.
*Scaphoid Protocols Using the Acutrak® Bone Screw System* brochure, Toby, published by Acumed, Inc., Dec. 7, 1999.
Single Unit Osteosynthesis brochure, Surfix Technologies, Sep. 2000.
Supracondylar Cable Plate brochure, Biomet Orthopedics, Inc., 2000.
Principle-Based Internal Fixation of Distal Humerus Fractures, Sanchez-Sotelo et al., *Techniques in Hand & Upper Extremity Surgery*, vol. 5, No. 4, pp. 179-187, Dec. 2001.
Congruent Plate System—The Mayo Clinic Congruent Elbow Plates brochure, Acumed, Inc., May 7, 2002.
Modular Hand System brochure, Acumed, Inc., Aug. 2002.
Modular Hand System brochure, Acumed, Inc., Sep. 2002.
Periarticular Plating System brochure, Zimmer, Inc., 2002.
Jplate Diaphysis Plates for Japanese brochure, Mizuho Co., Ltd., 2002.
An Axially Mobile Plate for Fracture Fixation, Abel et al., *Internal Fixation in Osteoporotic Bone*, pp. 279-283, 2002.
The Use of Interlocked 'Customised' Blade Plates in the Treatment of Metaphyseal Fractures in Patients with Poor Bone Stock, Palmer et al., *Injury, Int. J. Care Injured*, vol. 31, pp. 187-191, 2002.
3.5 mm LCP™ Proximal Humerus Plate technique guide, Synthes (USA), 2002.
Titanium Wire Plate Osteosynthesis System According to Dr. Gahr internet printout, Erothitan Titanimplantate AG, print date Feb. 6, 2003.
Bilder internet printout, Martin GmbH & Co. KG, print date Sep. 5, 2003.
International Search Report for PCT Patent Application Serial No. PCT/US03/22904, Dec. 4, 2003.
The Use of a Locking Custom Contoured Blade Plate for Peri-Articular Nonunions, Harvey et al., *Injury, Int. J. Care Injured*, vol. 34, pp. 111-116, 2003.
Salvage of Distal Tibia Metaphyseal Nonunions With the 90° Cannulated Blade Plate, Chin et al., *Clinical Orthopaedics and Related Research*, No. 409, pp. 241-249, 2003.
Rib Securing Clamped Plate internet printout, Sanatmetal, print date Sep. 22, 2004.

Acromio-Clavicular Plates description page, author and date unknown.
ECT Internal Fracture Fixation brochure, Zimmer, Inc., undated.
ECT Internal Fracture Fixation System order information brochure, Zimmer, Inc., undated.
NexGen Osteotomy System (OS) surgical technique brochure, Zimmer, Inc., undated.
Spider™ and Mini-Spider™ Limited Wrist Fusion System brochure, Kinetics Medical Incorporated, undated.
Spider™ Limited Wrist Fusion System brochure, Kinetics Medical Incorporated, undated.
Zueler Hook Plates description page, Codman & Shurtleff, Inc., p. 808, undated.
Biological Plating: A New Concept to Foster Bone Healing, Synthes (USA), 1991.
Treatment by Plates of Anteriorly Displaced Distal Radial Fractures, Ducloyer, *Fractures of the Distal Radius*, pp. 148-152, 1995.
Management of Comminuted Distal Radial Fractures, Jupiter et al., *Fractures of the Distal Radius*, pp. 167-183, 1995.
Open Reduction of Intra-Articular Fractures of the Distal Radius, Amadio, *Fractures of the Distal Radius*, pp. 193-202, 1995.
May Anatomical bone Plates: Plates, Bone Screws and Instruments brochure, pp. 3-4 and 10-15, Waldemar Link GmbH & Co., 1995.
Forte Distal Radial Plate System brochure, Zimmer, Inc., 1995.
Design and Biomechanics of a Plate for the Distal Radius, Gesensway et al., *Journal of Hand Surgery*, vol. 20, No. 6, pp. 1021-1027, 1995 (abstract only provided).
*Fractures of the Distal Radius: A Practical Approach to Management*, Fernandez et al., pp. 103-188, 1996.
Titanium Distal Radius Instrument and Implant Set standard contents description pages, Synthes, Mar. 1997.
Prospective Multicenter Trial of a Plate for Dorsal Fixation of Distal Radius Fractures, Ring et al., *The Journal of Hand Surgery*, vol. 22A, No. 5, pp. 777-784, Sep. 1997.
Treatment of Displaced Intra-Articular Fractures of the Distal End of the Radius With Plates, Fitoussi et al., *The Journal of Bone and Joint Surgery*, vol. 79, No. 9, pp. 1303-1312, 1997 (abstract only provided).
The Titanium Distal Radius Plate, technique guide, Synthes (USA), 1997.
TriMed Wrist Fixation System brochure, TriMed, Inc., 1997.
SCS/D Distal Radius Plate System brochure, Avanta Orthopaedics, 1997.
Intra-Articular Fractures of the Distal Aspect of the Radius, Trumble et al., *Journal of Bone and Joint Surgery*, vol. 80A, No. 4, pp. 582-600, Apr. 1998.
Complications of the AO/ASIF Titanium Distal Radius Plate System (π Plate) in Internal Fixation of the Distal Radius: A Brief Report, Kambouroglou et al., *Journal of Hand Surgery*, vol. 23A, No. 4, pp. 737-741, Jul. 1998.
SCS/V Distal Radius Plate Volar brochure, Avanta Orthopaedics, 1998.
Delayed Rupture of the Flextor Pollicis Longus Tendon After Inappropriate Placement of the π Plate on the Volar Surface of the Distal Radius, Nunley et al., *Journal of Hand Surgery*, vol. 24, No. 6, pp. 1279-1280, Nov. 1999.
TiMAX Pe.R.I. Small Fragment Upper Extremity description pages, DePuy ACE Medical Company, 1999.
The Distal Radius Plate Instrument and Implant Set technique guide, Synthes (USA), 1999.
Outcome Following Nonoperative Treatment of Displaced Distal Radius Fractures in Low-Demand Patients Older Than 60 Years, Young, *Journal of Hand Surgery*, vol. 25A, No. 1, pp. 19-28, Jan. 2000.
Comparison of Three Different Plating Techniques for the Dorsum of the Distal Radius: A Biomechanical Study, Peine et al., *Journal of Hand Surgery*, vol. 25A, No. 1, pp. 29-33, Jan. 2000.
Distal Radial Metaphyseal Forces in an Extrinsic Grip Model: Implications for Postfracture Rehabilitation, Putnam et al., *Journal of Hand Surgery*, vol. 25A, No. 3, pp. 469-475, May 2000.
TriMed Wrist Fixation System internet description pages, TriMed, Inc., 2001.
Titanium Distal Radius Plates description page, Synthes (USA), 2001.
Locon-T Distal Radius Plating System case study and surgical method, Wright Medical Technology, Inc., 2001.
Open Reduction and Internal Fixation of Unstable Distal Radius Fractures: Results Using the Trimed Fixation System, Konrath et al., *Journal of Orthopaedic Trauma*, vol. 16, No. 8, pp. 578-585, 2002.
Locon-T Distal Radius Plating System brochure, Wright Medical Technology, Inc., 2002.
Distal Radius Fracture, Tornetta, *Journal of Orthopaedic Trauma*, vol. 16, No. 8, pp. 608-611, 2002.
Comparison of Different Distal Radius Dorsal and Volar Fracture Fixation Plates: A Biomechanical Study, Osada et al., *Journal of Hand Surgery*, vol. 28A, No. 1, pp. 94-104, Jan. 2003.
*Tendon Function and Morphology Related to Material and Design of Plates For Distal Radius Fracture Fixation: Canine Forelimb Model*, Turner et al., Orthopaedic Research Society, Feb. 2003.
Fractures of the Distal Aspect of the Radius: Changes in Treatment Over the Past Two Decades, Simic, *Journal of Bone and Joint Surgery*, vol. 85-A, No. 3, pp. 552-564, Mar. 2003.
Palmar Plate Fixation of AO Type C2 Fracture of Distal Radius Using a Locking Compression Plate—A Biochemical Study in a Cadaveric Model, Leung et al., *Journal of Hand Surgery*, vol. 28B, No. 3, pp. 263-266, Jun. 2003.
Functional Outcome and Complications Following Two Types of Dorsal Plating for Unstable Fractures of the Distal Part of the Radius, Rozental et al., *Journal of Bone and Joint Surgery*, vol. 85, No. 10, pp. 1956-1960, 2003 (abstract only provided).
*Fixation of Unstable Fractures of the Volar Rim of the Distal Radius with a Volar Buttress Pin®*, Hooker et al., 2003.
Results of Palmar Plating of the Lunate Facet Combined with External Fixation for the Treatment of High-Energy Compression Fractures of the Distal Radius, Ruch et al., *J. Orthop. Trauma*, Vo. 18, No. 1, pp. 28-33, Jan. 2004.
Synthes Volar Distal Radius Locking Plate internet description page, Orthocopia, LLC, 2004.
VAL Plate description page, US Implants, undated.
Esser Complete Distal Radius Plate System, undated.
Proximal Humerus Fractures operative technique, Esser, undated.
Biomechanical Evaluation of the Schuhli Nut, Kolodziej, et al., *Clinical Orthopaedics and Related Research*, vol. 347, pp. 79-85, Feb. 1998.
Internal Fixation in Osteoporotic Bone, An, Y.H., p. 83, 2002.
Zespol Bone Screws, in *Mikromed—Catalogue* 2004 (Nov. 2004), available at http://www.mikromed.pl/katalog/Main/main_eng.htm and http://www.mikromed.pl/katalog/zespol_eng/wkrety.htm.
Zespol Bones Plates, in *Mikromed—Catalogue* 2004 (Nov. 2004), available at http://www.mikromed.pl/katalog/Main/main_eng.htm and http://www.mikromed.pl/katalog/zepol_eng/plytki.htm.
SmartLock Locking Screw Technology, advertisement, *The Journal of Hand Surgery*, vol. 30A, No. 1, Jan. 2005.
MIfx Dorsal IM Plate, brochure, DVO Extremity Solutions, Sep. 2005.

\* cited by examiner

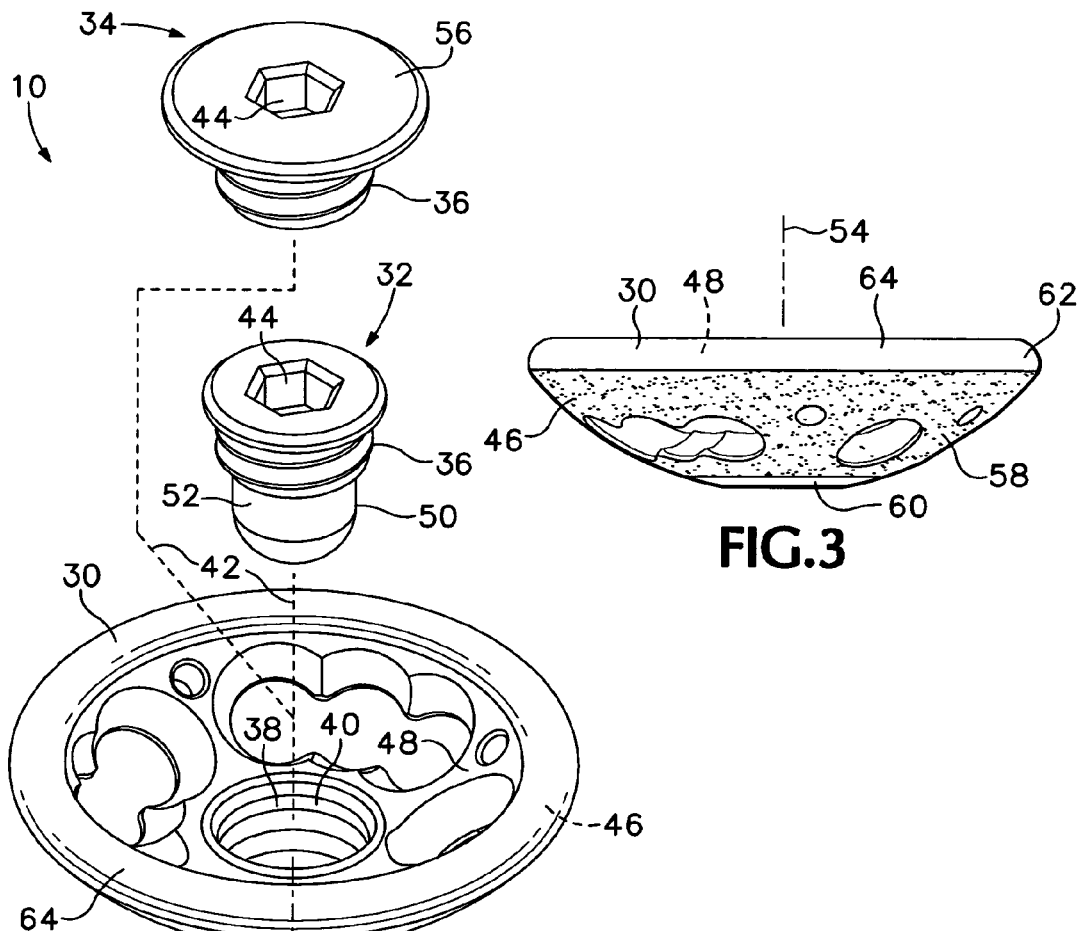
FIG.2
FIG.3
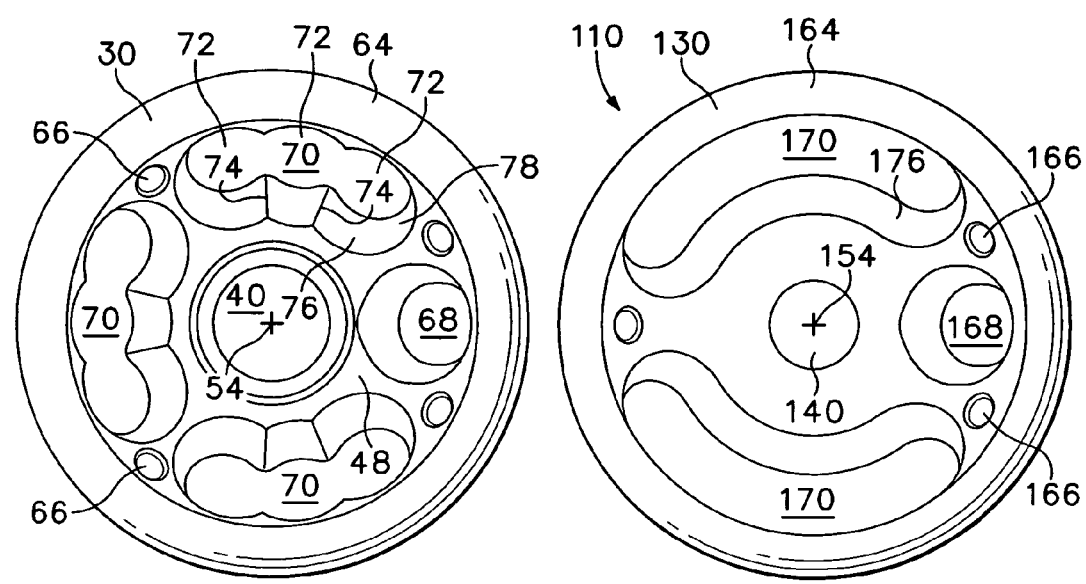
FIG.4
FIG.5

BONE FUSION SYSTEM

CROSS-REFERENCES

This application is based upon and claims the benefit under 35 U.S.C. § 119(e) of the following U.S. provisional patent applications: Ser. No. 60/398,075, filed Jul. 22, 2002; and Ser. No. 60/484,262, filed Jun. 30, 2003. Each of these provisional patent applications is incorporated herein by reference in their entirety for all purposes.

FIELD OF THE INVENTION

The invention relates to bone plates. More specifically, the invention relates systems for fusing two or more bones with a bone plate.

BACKGROUND

Bone plates are devices for fixing bone, to facilitate repair of individual bones or joining of adjacent bones. Most commonly, bone plates are used to fix bone discontinuities, such as fractures or osteotomies, in individual bones. To fix such a bone discontinuity, a bone plate is attached to opposing sides of the discontinuity so that fragments of the affected bone can be held and/or grow together to repair the bone. However, in some cases, bone plates are used to join distinct bones at articular ends of the bones. For example, some articular injuries and/or diseases are treated effectively by bone fusion with a bone plate. Cartilage that separates articulating bones is removed, and a bone plate is attached. The plate spans a junction between the bones to fix the bones in close apposition so that the articular ends of the bones can fuse through bone growth.

The hand is a common site for performing bone fusion, for example, to treat osteoarthritis. Typically, four of the carpal bones are fused so that these bones can no longer move relative to one another. A bone plate for fixing carpal bones during and after bone fusion is disclosed in U.S. Pat. No. 6,179,839 to Weiss et al., issued Jan. 30, 2001 (the "Weiss patent"), which is incorporated herein by reference. The Weiss patent provides a substantially conical bone plate that is attached with bone screws at the junction of four carpal bones. The junction is modified prior to plate attachment to include a matching conical recess, by removing a portion of each carpal bone. The fusion plate is placed in the conical recess and attached to recessed bone surfaces to dispose the plate in a less obtrusive position below the anatomical surfaces of the carpal bones. The cone angle of the conical plate may help to direct the screws at oblique angles relative to the anatomical surfaces of the carpal bones and in a generally radial pattern from the plate. As a result, the bone screws pull the carpal bones together around the bone plate, as the screws attach the plate to the carpal bones.

The bone plate disclosed in the Weiss patent ("the Weiss plate") has a variety of shortcomings. For example, the Weiss plate lacks an effective mechanism for holding the plate in contact with the recessed bone surfaces as the bone screws attach the plate to the carpal bones. Accordingly, the Weiss plate has a tendency to move (e.g., pivot and/or translate) out of full contact with the recessed bone surfaces when a load is applied unevenly to the plate, such as when the first bone screw attaches the plate to bone. As a result, the Weiss plate may be attached so that the plate is shifted from its desired target position. In addition, the Weiss plate lacks openings that allow optimal placement of a bone screw into each target carpal bone. Accordingly, a surgeon using the Weiss plate may be unable to secure one or more of the target carpal bones to the plate, because the plate has openings that are spaced too widely from one another. Furthermore, the Weiss plate lacks a mechanism to prevent bone screws from backing out of their inserted positions, for example, when inserted into bone of poor quality. Accordingly, some of the bone screws that are intended to hold the plate in position may back out of full engagement with bone, resulting in irritation of soft tissue that overlies the plate. The Weiss plate also may be configured to be placed more deeply into bone than is necessary, because of the conical shape of the Weiss plate.

SUMMARY OF THE INVENTION

The invention provides systems, including apparatus, methods, and kits, for fusing two or more bones with a bone plate.

BRIEF DESCRIPTION OF THE DRAWINGS

FIG. 2 is an exploded view of the bone plate of FIG. 1, showing a body portion, and a post portion and a cap that may be coupled to a centrally positioned opening of the body portion, in accordance with aspects of the invention.

FIG. 3 is a side elevation view of the body portion of FIG. 2, in accordance with aspects of the invention.

FIG. 4 is a top plan view of the body portion of FIG. 2, in accordance with aspects of the invention.

FIG. 5 is a top plan view of an alternative bone plate for joining a plurality of bones, in which the bone plate has an integral post, in accordance with aspects of the invention.

DETAILED DESCRIPTION

Figure 1:
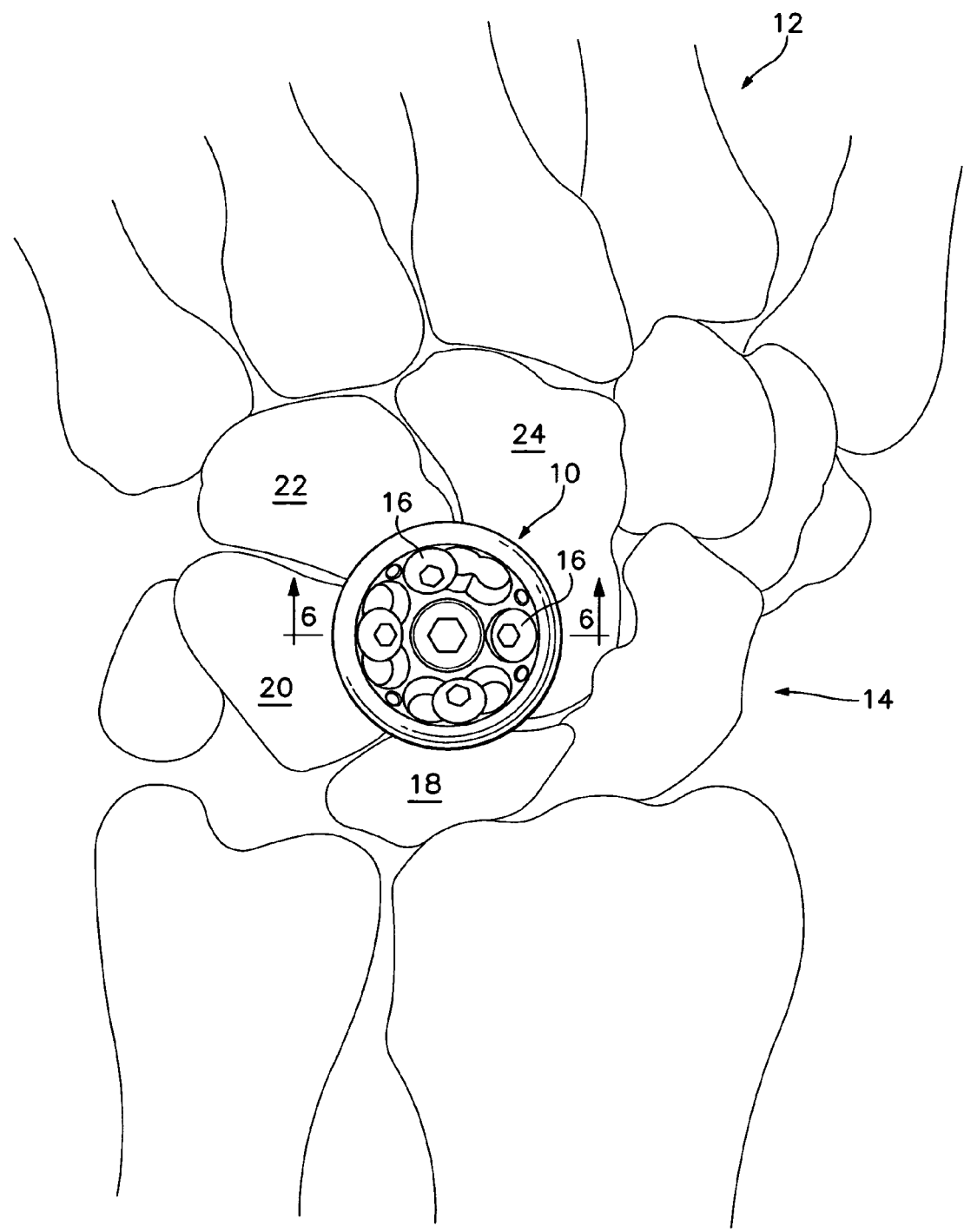
FIG. 1 is an environmental view of a bone plate joining a plurality of carpal bones of the left hand, in accordance with aspects of the invention.

The invention provides systems, including apparatus, methods, and kits, for fusing two or more bones with a bone plate. The bone plate may include (1) a body portion configured to be received by a recess in one or more of the bones, and (2) one or more features to facilitate improved positioning and/or attachment of the body portion to the bones (and/or improved comfort or function), including a projection, a cap, an opening, a rough bone-facing surface, and/or a thickened perimeter, among others. These and other aspects of the invention are described, in detail, in the following sections: (I) bone plate, and (II) examples.

I. Bone Plate

The bone plate may be configured to join at least two bones or portions thereof. The bone plate may include a body portion configured to be received by a recess defined by recessed surfaces at a junction region of two or more bones (the target bones), such as bones of the hand or foot. The recess and the recessed surfaces typically are formed by removing or excavating bone material from the bones (such as by reaming the bones) at the junction region. The recessed surfaces may be at least substantially complementary to a bone-facing surface of the body portion of the bone plate. Accordingly, the bone-facing surface of the body portion may be convex, to contact the recessed surfaces when inserted into the recess and positioned for attachment to the recessed surfaces. The bone-facing surface of the body portion may have any suitable shape, including at least substantially hemi-spherical, conical, and/or cylindrical, among others; in some embodiments, the body portion may include a generally planar annular region.

A hemi-spherical bone-facing surface may have a number of advantages over a conical bone-facing surface. The hemi-spherical bone-facing surface (and/or body portion) may increase the amount of surface area that contacts bone relative to a conical surface. Accordingly, such a hemispherical surface and/or body portion may be configured to be placed more shallowly into bone that a conically shaped body portion, resulting in a less-invasive placement that preserves more of the native bone. Any tendency to wobble imparted by the hemispherical bone-facing surface or body portion may be counteracted with fasteners and/or an optional post.

The bone plate further may include one or more features to facilitate improved positioning and/or attachment of the body portion to the bones, and/or to increase comfort for a recipient of the bone plate. These features may include (A) a projection that extends from the bone-facing surface on or adjacent a central region of the plate portion, (B) a cap to obstruct movement of fasteners out of bone, (C) an opening (and/or a distinctive combination of openings) through which bone fasteners, such as bone screws, may be inserted for attaching the bone plate to the bones, (D) a rough texture on a region of the bone-facing surface, and/or (E) a thickened perimeter on the body portion, among others. Any combination of these and other features described herein may be included in a body portion of any suitable shape to form a bone plate.

The bone plate may have a projection, such as a post, that is joined to or that extends beyond a bone-facing surface of a central region of the body portion. The projection may be received by a hole defined by one or more of the target bones. This hole, and recessed bone surfaces defining a recess surrounding the hole, may be formed by removing bone material from the bones at the junction region. The hole may be centered in the recess at the junction of the bones. Contact between the projection and bone surfaces that define the hole may restrict movement of the body portion, such as tilting and/or translation out of alignment with the recess, during and/or after attachment of the body portion to bone. The projection may be a separate component, for example, threaded or otherwise inserted in an opening in the body portion, or it may be formed unitarily with the body portion.

The bone plate may include a cap that can be coupled to the body portion before or after the body portion has been secured to the target bones. The cap may restrict movement of one or more of the inserted bone fasteners out of bone, while the body portion is attached to bone. Thus, the cap may prevent loosened fasteners from irritating or injuring a recipient of the plate.

The bone plate may include one or more different types of openings that increase options for attaching the plate to bone. The openings may include circular holes (i.e., openings characterized by a single diameter), and/or elongated holes, such as grooves or slots (i.e., openings characterized by a length and width), among others. The elongated holes may include compression slots that extend radially outward from a central region of the plate, and/or arcuate slots that extend partially circumferentially around a central region of the plate, among others. Alternatively, or in addition, the openings may include smaller apertures for wires and/or pins, one or more openings for inserting single fasteners, and/or one or more multi-site openings for inserting a bone fastener at one of plural discrete positions within the multi-site opening. The edges of the openings may have any suitable form, including smooth, scalloped, straight, beveled, unthreaded, threaded, symmetric, and/or asymmetric, among others.

The bone plate may include other features that relate to the texture and/or geometry of the plate. For example, the plate may have a rough texture on its bone-facing surface, for example, to facilitate contact and/or fusion with bone. Alternatively, or in addition, the plate may have a thickened outer edge at the perimeter of the body portion to minimize irritation of soft tissue.

The bone plate, that is, the body portion and ancillary components (e.g., projection, cap, fasteners, etc.) generally may be formed of any suitable biocompatible material, such as stainless steel, titanium (or an alloy thereof), cobalt chromium, ceramic, a bioabsorbable (resorbable) material, and/or the like.

II. EXAMPLES

The following examples describe selected aspects and embodiments of the invention. These examples are included for illustration and are not intended to limit or define the entire scope of the invention.

II.A. Example 1

This example describes several exemplary bone plates, as well as methods for attaching the bone plates to suitable bones.

FIG. 1 shows an embodiment of a bone fusion device, bone plate 10, fixing and joining plural bones of a left hand 12. Plate 10 may be attached to carpal bones 14 of hand 12 using plural fasteners, such as bone screws 16. Each bone screw 16 may be directed into one (or more) of a plurality of carpal bones, in this case, four carpal bones. Here, plate 10 is attached to a lunate bone 18, a triquetrum bone 20, a hamate bone 22, and a capitate bone 24. The shafts of the bone screws may extend into the bones so that the shafts are oblique to the plane of the hand (see below). Accordingly, the bone screws may help to prevent separation of the plate from the bones along an axis orthogonal to the plane of the hand, and the screws may pull the bones together, generally toward one another, for example, by compressing the bones radially towards a central axis of plate 10. Plate 10, more generally, may be configured and used to fix and/or join any suitable combination of at least two or more, and more typically three or more adjacent bones of the carpus, another region of the hand, the foot, and/or any other suitable region of the skeleton.

FIG. 2 shows an exploded perspective view of bone plate 10. Plate 10 may include a body or body portion 30, a post portion 32, and/or a cap 34. Post portion 32 and/or retaining cap 34 may be configured to be attached to body portion 30.

For example, one or both may include a threaded portion 36 that couples to complementary threads 38 defined at the perimeter of a central opening 40 or hole of body portion 30. Here, post portion 32 and retaining cap 34 may be attached alternatively to body portion 30, as shown at 42 by the dashed lines. Generally, post portion 32 may be attached first, before bone screws are inserted into bone, by rotational engagement of post portion 32 with body portion 30, for example, by using a tool to rotate post portion 32 by contact with tool-gripping structure 44. Cap 34 may replace post portion 32 in central opening 40 after bone screws have been inserted into bone. Alternatively, body portion 30 may be configured to have a central opening that is nonthreaded. Accordingly, the bone plate may lack post portion 32 and/or cap 34, and/or may couple one or both to body portion 30 by another mechanism.

Body portion 30 includes a bone-facing or bone-facing surface (or side) 46 and a bone-opposing surface (or side) 48. The surfaces may oppose one another to have distinct spatial and/or functional relationships to bone, bone fasteners, and/or overlying soft tissue. The bone-facing surface 46 may at least substantially match and contact a first portion (or all) of recessed bone surfaces formed in bones at an inter-bone junction or movable joint. In contrast, bone-opposing surface 48 may be configured to face at least substantially away from bones at the junction. Accordingly, bone-opposing surface 48 may contact the head of bone screws or other fasteners to restrict plate movement, that is, wobble or translational movement of bone-facing surface 46 relative to the recessed bone surfaces. In addition, bone-opposing surface 48 may face and be disposed closer to soft tissue that overlies the recessed bone surfaces.

Body portion 30 may have any suitable overall shape and size. The length and width of body portion 30 may be at least substantially equal (measured across the perimeter of the body portion), corresponding to a circle, as shown here, a regular polygon, and so on. Alternatively, the length and width may be different, together defining an ellipse, an oval, an irregular polygon, and so on. The height of the body portion (measured from the bottom to the top of the plate as disposed in FIG. 3) may be preferably less than the length and/or width, to form a relatively shallow body portion. The thickness of the body portion, measured locally between opposing surfaces 46, 48, preferably is substantially less than the length, width, and height. Accordingly, the body portion may be considered a shell. The body portion has a shape and thickness generally determined by opposing surfaces 46, 48, as described further below.

Post portion 32 generally comprises any protruding structure or projection, such as post 50 that extends from bone-facing surface 46 toward bone. The projection may be configured to act as a positioning structure or partial anchor for body portion 30 within a hole or recess (see also discussion of FIG. 6 below). Post portion 32 may be disposed at a central region of the body portion, for example, in central opening 40, and may be removable, attached permanently, or formed integrally. As a positioning structure, post 50 may contact bone in a hole to restrict tilting and/or translational movement of body portion 30 away from a centered position, relative to the recessed bone surfaces that the plate contacts.

The post may be configured to restrict movement of body portion 30 by contact with a hole formed within the bone recess at an inter-bone junction. The hole may be deeper in bone, for example, farther below anatomical bone surfaces, than the recessed bone surfaces of the recess that contact and/or adjoin adjacent bone-facing surface 46 of body portion 30. As a result, insertion of the post into the hole restricts plate movement through contact of a projection surface 52 with the hole in bone.

Projection surface 52 may have any suitable shape that contacts the hole to restrict plate movement. In some embodiments, projection surface 52 is at least substantially complementary to a hole formed in bone, generally formed by a rotating tool. Thus, projection 50 and projection surface 52 may have a shape based on a circle, such as cylindrical, hemi-spherical, conical, a combination thereof, and/or the like. Throughout this document, the term "hemi-spherical" is intended to mean any portion of a sphere including but not necessarily comprising exactly half a sphere. For example, a hemi-spherical projection (or hemi-spherical bone-facing surface) may be literally half of a sphere, less or more than half of a sphere, a frustum of a sphere, or any other suitable portion of a sphere. A hemi-spherical surface or structure may correspond substantially to a spherical cap, that is, a planar truncation of a sphere. The term conical is intended throughout to mean a portion of a cone, such as a frustoconical region, a region of a cone between nonparallel planes, an end portion of a cone defined by a single plane intersecting a cone, multiconical (formed of frustoconical and/or conical portions with distinct cone angles), and/or the like. Alternatively, the hole in bone and projection surface 52 may have other complementary shapes or may be only partially complementary (see discussion of FIG. 6 below). For example, projection surface 52 may have a polygonal cross section that mates with a cylindrical hole.

A post (or projection) may have any suitable location on, and structural relationship with, body portion 30. For example, the post may be positioned generally in a central region of body portion 30. In some embodiments, the post may be substantially coaxial with body portion 30, so that central axis 54 of the body portion is aligned substantially with a corresponding central axis of the post. Alternatively, the post (or plural posts) may extend along an axis distinct from central axis 54. The distinct axis may be parallel or nonparallel to central axis 54. The post may be provided by a separate removable component, such as in plate 10, may be a separate component that is permanently attached to the body portion after fabrication of the body portion, or may be formed unitarily with the body portion, that is, so that the body portion and the post are a single piece (see FIGS. 5 and 7).

Cap 34 may have any suitable structure that obstructs movement of fasteners, received by the body portion, out of bone. Accordingly, the cap may be a separate component that is attached to the body portion after insertion of one or more fasteners, such as bone screws, into bone. Cap 34 may have a blocking portion or head 56 that has a larger diameter than threaded portion 36 of the cap. Blocking portion 56 may be configured to overlie bone-opposing surface 48 of body portion 30 and partially or completely overlie heads of fasteners received by the body portion (see FIGS. 6B and 7).

FIG. 3 shows bone-facing surface 46 of body portion 30 in a side elevation view of the plate. Bone-facing surface 46 may be convex. Convex, as used herein, means that the surface bulges generally outward so that it can be received in a bone recess. However, the convex surface may include local variations that are concave are planar, such as dimples. Bone-facing surface 46 may have a substantially hemi-spherical shape, as defined above, here corresponding to a frustum of a sphere. In some embodiments, the bone-facing surface may correspond at least substantially to a spherical cap. However, other circle-based shapes may be suitable, such as conical (see above), among others. In some embodiments, bone-reaming strategies that form non-circular shapes defined by recessed bone surfaces, such as ovals, may allow bone-facing surface 46 to be formed with any substantially complementary shape to the recessed bone surfaces, or portion(s) thereof.

FIG. 3 shows a rough region 58 on bone-facing surface 46. Rough region 58 has a rough and/or porous texture that may extend over some or all of bone-facing surface 46. Here, rough region 58 is restricted to a hemispherical segment flanked by smooth regions 60, 62. However, in alternative embodiments, rough region 58 may extend over any suitable portion of surface 46. The rough and/or porous texture of rough region 58 may enable bone attachment by bone growth onto bone-facing surface 46. By contrast, other bone plates typically have smooth, polished surfaces that are not conducive to bone attachment by bone ongrowth. Accordingly, rough region 58 has a texture that is relatively rough, that is, rough relative to a typical bone plate surface or to the opposing surface of body portion 30. Rough region 58 and a typical bone plate surface (or bone-opposing surface 48 of body portion 30) may be palpably distinguishable, that is, by feel, for example, by differences in the ease with which a person's skin slides over rough and smooth surfaces, among others. The rough region may be distinguishable also or alternatively by sight, for example, by differences in the way in which rough and smooth surfaces reflect light, or functionally, for example, by an enhanced ability to support bone attachment, among others. Rough region 58 may be formed during and/or after formation of body portion 30, for example, by removing, and/or adding material to the surface of the body portion, and/or by structuring the material at the surface. Exemplary procedures for forming region 58 may include casting, particle (grit) blasting, grinding, sanding, spraying, dipping, milling, stamping, molding, and/or the like.

The body portion of a bone fusion plate, such as body portion 30, may have any suitable thickness(es). For example, the body portion may have a generally uniform thickness, measured between opposing surfaces 46, 48, so that bone-opposing surface 48 has a substantially concave shape that is generally complementary to bone-facing surface 46. Alternatively, the thickness may vary so that surfaces 46, 48 have different shapes. For example, the thickness of body portion 30 may be increased at the perimeter of the body portion, that is, near rim or outer edge 64, which joins surfaces 46, 48 at their perimeters. A thickened perimeter means that the plate has a greater thickness near or at outer edge 64 than the average thickness of the body portion. Outer edge 64 preferably is rounded, with a local diameter that defines the outer edge thickness (see FIG. 6). Thickened outer edge 64 may minimize tendon irritation as tendons slide over outer edge 64 of bone-attached body portion 30 and/or may increase the strength of body portion 30. Alternatively, or in addition, body portion 30 may taper in thickness toward outer edge 64 and/or toward central axis 54.

FIGS. 4 and 5 show plan views of body portion 30 and another embodiment of a bone plate 110 having an alternative body portion 130. Body portion 30 or 130 may include various types of openings or recesses: central opening (hole) 40 or central recess (hole) 140 (described above or below), and laterally disposed openings for fasteners, among others. In some embodiments, the central opening may be configured to receive a fastener to fasten the body portion to bone. Fasteners generally include any mechanism for affixing the plate to bone. Exemplary fasteners include bone screws, wires, hooks, and/or pins, among others.

Fastener openings on a plate generally extend between opposing surfaces of the plate and may have any suitable position, size, shape, and/or frequency. Openings may be disposed laterally from a central region of the body portion, at a single distance or plural distances from central axis 54 or 154. The openings may be disposed in a radially symmetrical or asymmetrical pattern. Furthermore, one or plural openings may be disposed along a single radial path of the plate, from the central axis to the outer edge. A plate may include openings of one size or of distinct sizes, for example, to receive fasteners of distinct diameter. Openings may be configured to receive one or plural fasteners, either at one or a plurality of positions within each opening. Openings may be bounded by tapered edges that define counterbores. Counterbore surfaces are generally included in bone-opposing surface 48. The counterbores may be configured to position the plate as the fasteners are tightened, for example, guiding the counterbore surfaces into abutment with a head portion of each fastener and/or sliding the bone plate relative to the fastener (such as with a compression slot). Each opening may include one or plural counterbores. Plural sub-openings may overlap partially to form an elongate opening or slot. Exemplary fastener openings may include small apertures 66, 166, fixed-position opening(s) 68, 168, and/or slots 70, 170, among others. Other exemplary openings and arrangements of openings are described below in relation to FIG. 9.

Small apertures 66, 166 may receive small-diameter fasteners. A small aperture is any opening that has a smaller diameter than an opening configured to receive a bone screw. Accordingly, small-diameter openings may be suitable for wires, such as K-wires, and/or pins. Any suitable number of small apertures may be formed in body portion 30, 130, but preferably at least two. Moreover, the small apertures may be disposed at equal or unequal distances from central axis 54 or 154 and may be closer, equal to, and/or farther in distance from the central axis than single-position openings 68, 168 and/or slots 70, 170. Fasteners placed in small apertures 66, 166 may be suitable, for example, to attach body portion 30, 130 provisionally to bone and thus limit movement of the plate. With the plate held provisionally in place by wires, larger holes for bone screws may be drilled in target bone, and/or the bone screws may be placed into bone through opening 68, 168 and slots 70, 170.

Fixed-position openings 68, 168 may be dimensioned to receive only one fastener, such as a bone screw. Opening 68, 168 may be substantially circular to define a relatively fixed position at which a bone screw attaches the bone plate to bone. In the exemplary embodiments shown, body portion 30 or 130 includes only one fixed-position opening 68 or 168 for attaching a bone screw to bone at a substantially predefined circumferential position of the plate, although a plurality of such openings may be included. In preferred methods of using the bone plate, a bone screw is introduced into bone through opening 68 or 168 before selecting sites for attachment to bone using slots 70, 170 (see below).

The body portion of the bone plate may include one or more slots 70, 170. The slots may have any suitable shape and disposition. Each slot may be linear, arcuate, curvilinear, or a combination thereof, among others. The slot may extend along generally radial paths from the central axis or central region of the plate (see FIG. 8), or may extend along a path that is spaced from the central axis or region (see FIGS. 4 and 5). For example, the slot may extend partially around the central axis of the body portion and thus may be arcuate when viewed from generally normal to the bone-opposing surface. Accordingly, the slot may define an arc that forms part of a circle. The circle may be at least substantially orthogonal to the central axis and centered at the central axis. Alternatively, the slot be linear and extend substantially tangentially from a circle defined by the bone plate. The slot may be disposed distinctly from a standard compression slot, for example, opening 70, 170 may extend in a direction distinct from (and generally orthogonal to) the direction in which underlying bone may be pulled by tightening bone screws.

Each slot may be dimensioned to receive one or more fasteners at plural sites along the long axis of the slot. The plural sites may be discrete, that is, the sites may be configured to be distinguishable and finite in number. For example, in body portion 30, each slot 70 has three discrete fastener-receiving sites 72, in this case, configured to receive one fastener each. However any number of sites may be suitable. Each receiving site 72 may be used to position body portion 30 in contact with the head portion of a bone fastener, generally using nonoverlapping regions of bone-opposing surface 48. Alternatively, the plural sites may be continuous instead of discrete, thus providing a continuum of potential fastener-receiving sites. For example, each slot 170 of body portion 130 is not divided into discrete receiving sites, and thus the head portion of a bone screw may be positioned at any desired position along the slot. In either case, the slot may be configured to receive fasteners at discrete (openings 70) or a continuous (openings 170) set of positions within the slot.

Fastener-receiving sites 72 may have any suitable configuration that produces discrete sites. For example, sites 72 may be separated by stops 74, generally in the form of narrowed regions (widthwise) of slot 70 on one or generally opposing surfaces of edge 76. The stops 74 may restrict plate movement, for example, rotational movement about central axis 54. When a fastener is partially and/or completely inserted at one of sites 72, contact between the fastener and the stops or narrowed regions may prohibit plate movement. Stops may take the form of teeth, ridges, and/or other suitable projections that extend from edge 76, generally toward slot 70. The stops may be configured to limit plate movement by contact between a head portion of the bone screw as the bone screw is inserted into target bone. By contrast, a shaft portion of the bone screw apposed to edge 76 may not limit plate movement substantially, for example, allowing the shaft portion to be moved between each of the sites 72 of a slot 70. The stops may be defined by counterbores 78 configured to contact the head portion of the bone screw as the head portion contacts the body portion on bone-opposing surface 48, when fully inserted into bone. Accordingly, each site 72 also may be defined by a distinct counterbore 78 formed by edge 76.

Fastener-receiving sites 72 may be dimensioned so that fasteners cannot be fully inserted into bone in adjacent sites 72 of slot 70. For example, each slot 70 may receive a bone screw in the central site 72 of slot 70, in one or both of the flanking sites of slot 70, but may not receive bone screws in one or both of the flanking sites and in the central site concurrently. When bone screws are inserted into bone in a flanking and central site concurrently, the shafts of the bone screws may not interfere with one another, but both heads of the bone screws may be unable to fully contact edge 76 at adjacent counterbores 78. In some embodiments, slot 70 may be configured to receive only one fastener at one of plural discrete sites 72.

FIG. 1 shows an exemplary use of slots to attach bone plate 10 to different bones using fasteners received through each opening. In this illustration, a suitably positioned fastener-receiving site in each slot has been selected for attaching the plate to each of the four carpal bones, generally after the fixed-position opening has received a bone screw that attaches plate 10 to bone 24. Accordingly, a central fastener-receiving site has been used to attach the plate to bones 18, 20, and a lateral fastener-receiving site has been used to attach to bone 22.

Slot 170 may allow bone screws or other fasteners to be inserted at any suitable position along the opening (see FIG. 5). In contrast to slot 70 (FIG. 4), slot 170 lacks stops that contact the head of the bone screw to restrict rotational movement of the plate. Instead, slot 170 may restrict rotation by frictional contact with any region of edge 176 that is juxtaposed to the head of an inserted bone screw, as the screw is tightened against the region.

Figure 6A:
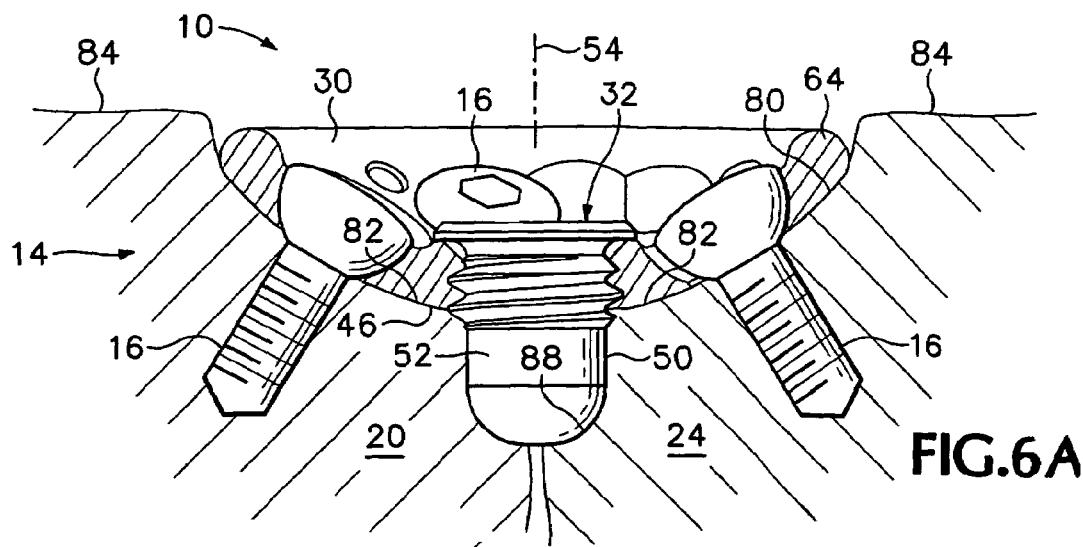
FIG. 6A is a sectional view of the bone plate and carpal bones of FIG. 1, viewed generally along line 6—6 of FIG. 1, in accordance with aspects of the invention.

FIG. 6A shows a sectional view of bone plate 10 joining carpal bones 14 of the left hand. Body portion 30 is received in a recess 80 defined by recessed surfaces 82 of carpal bones 14, with outer edge 64 disposed at or below anatomical surface 84 of the bones and generally parallel to the anatomical surface. Recess 80 (and the hole adjoining recess 80 and described below) may be produced, for example, during surgery by drilling, reaming, burring, and/or the like, using a single-step or multi-step bone-removal process. Although described as one recess, recess 80 preferably is formed by plural recessed surfaces 82 that are contributed by each of the target bones to be fused. Accordingly, in some embodiments, recess 80 may include a slight gap(s) 85 at bone junctions.

Recessed surfaces also may form a deeper hole 88 central to recess 80. Hole 88 may be configured to receive projection 50 and contact projection surface 52. Recessed bone surfaces that that define hole 88 may be configured to contact both the cylindrical side walls and the bottom of projection 50, as shown here. Alternatively, hole 88 may extend more deeply into bone than a bottom portion of projection 50, so that the bottom portion of projection 50 is spaced from the bottom of the hole. In this case, only the side walls of projection 50 may contact recessed bone surfaces defining hole 88. In some cases, hole 88 may be a through-hole that lacks a bottom, rather than a recessed region.

Contact between projection surface 52 and recessed bone surfaces of hole 88 may restrict movement of body portion 30. In particular, the body portion may be restricted from moving side-to side, that is, generally parallel to anatomical surface 84 and/or parallel to a plane defined by outer edge 64, and/or restricted from pivotal movement that changes the pitch of the plate relative to anatomical surface 84. Movement parallel to central axis 54 may be unrestricted until fasteners are received in the openings of body portion 30.

FIG. 6A shows bone screws 16 extending obliquely into bone, that is, oblique to anatomical surface 84 and to a bone axis orthogonal to anatomical bone surface 84. This oblique angle may pull the plate toward bone parallel to the bone axis and central axis 54, to promote attachment of the bone to the plate. In addition, the oblique angle may pull the bones together or toward one another to promote fusion. Pulling the bones together may result in radial compression of the bones. Accordingly, bone plates described herein may have any suitable structure that allows this oblique placement of bone screws and/or causes the bones to be pulled together when bone screws attach the plate to bone.

Figure 6B:
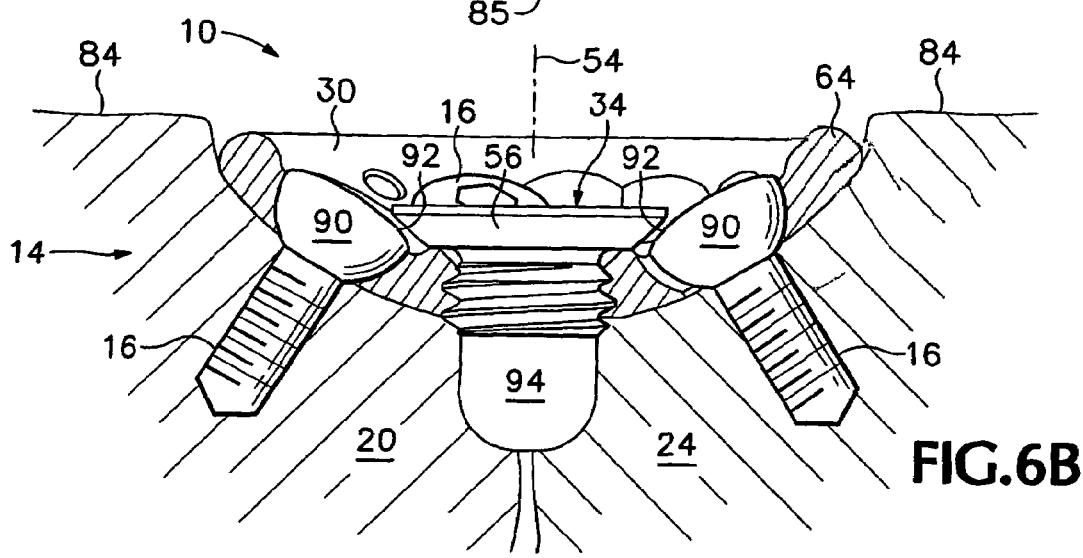
FIG. 6B is another sectional view of the bone plate and carpal bones of FIG. 1, viewed generally along line 6—6 of FIG. 1, but showing an alternative configuration of the bone plate in which the post portion has been replaced with the cap of FIG. 2, in accordance with aspects of the invention.

FIGS. 6A and 6B show a differential effect of post portion 32 and cap 34 on the ability of bone screws 16 to move out of bones 20, 24. FIG. 6A shows that a top portion of post portion 32 has a diameter that does not obstruct movement of inserted bone screws 16, along their long axes, out of bone. Accordingly, bone screws 16 may be fully inserted into bone and fully removed from bone while post portion 32 is in place. By contrast, FIG. 6B shows that cap 34 may have a blocking portion 56 with a larger radius than the radial distance from central axis 54 to head 90 of each bone screw 16. Accordingly, blocking portion 56 may restrict disengaging (out-of-bone) movement of some or all bone screws 16 along their long axes. Thus, cap 34 generally is connected to the body portion after the bone screws have been placed into bone. For example, cap 34 may be received in a central hole (through-hole or recess) from bone-opposing surface 48. Here, cap 34 is configured to contact a top region 92 of each head 90. In alternative embodiments, cap 34 may be configured to contact any suitable region of the fastener(s) to obstruct movement of the fastener(s) out of bone. Cap 34 may be spaced from head 90 when coupled to body portion 30, as shown in FIG. 6B, to allow some variation in fastener head size, head geometry, and/or angle of fastener insertion, and/or the like. Accordingly, in some embodiments, a fully inserted fastener may move partially out of bone before further disengaging movement along the fastener's long axis is restricted by blocking portion 56 of cap 34. Therefore, cap 34 may restrict movement of one or more bone fasteners completely out of bone, and more preferably, before the one or more fasteners project above a plane defined by outer edge 64.

Cap 34 may be configured to include or lack a post. Here, cap 34 lacks post 50, so that replacement of post portion 32 with cap 34 leaves a void 94. Void 94 may be filled with bone chips or other suitable filler material at any appropriate time, particularly after post portion 32 is removed and before cap 34 is attached. Alternatively, void 94 may be left unfilled, or, if the projection is not to be used, not formed at all.

Figure 7:
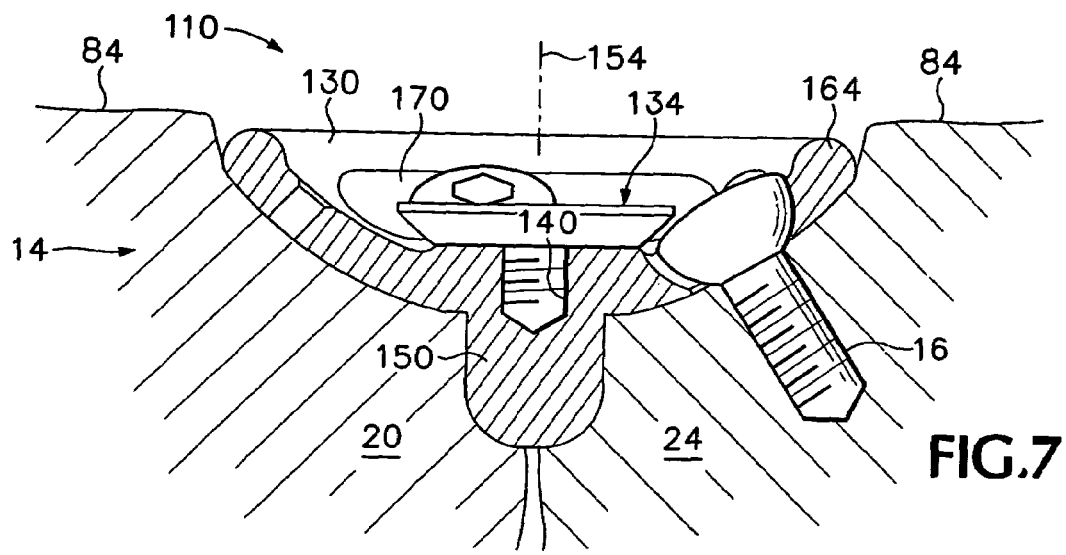
FIG. 7 is a sectional view of the bone plate of FIG. 5, viewed and attached to carpal bones generally as in FIGS. 6A and 6B, in accordance with aspects of the invention.

FIG. 7 shows alternative bone plate 110 (see FIG. 5) joining a plurality of carpal bones. Plate 110 includes body portion 130 with an integral post 150. Integral post 150 may be formed unitarily with body portion 130, that is, as one piece that includes both the post and body portion. Cap 134 may be attached to body portion 130 by threadable engagement with a central recess 140 (or through-hole) that is formed, for example, in alignment with central axis 154. In alternative embodiments, the body portion may lack a central recess, a central opening, and/or a post/projection.

Figure 8:
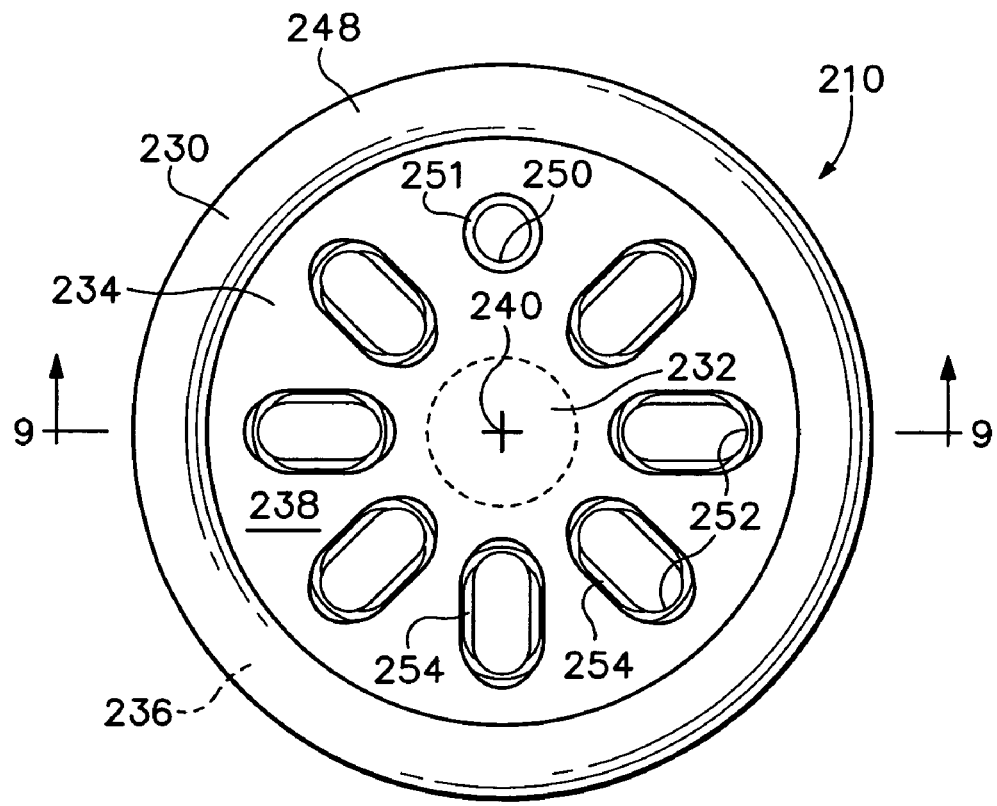
FIG. 8 is a top plan view of another bone plate for joining a plurality of bones, in accordance with aspects of the invention.
Figure 9:
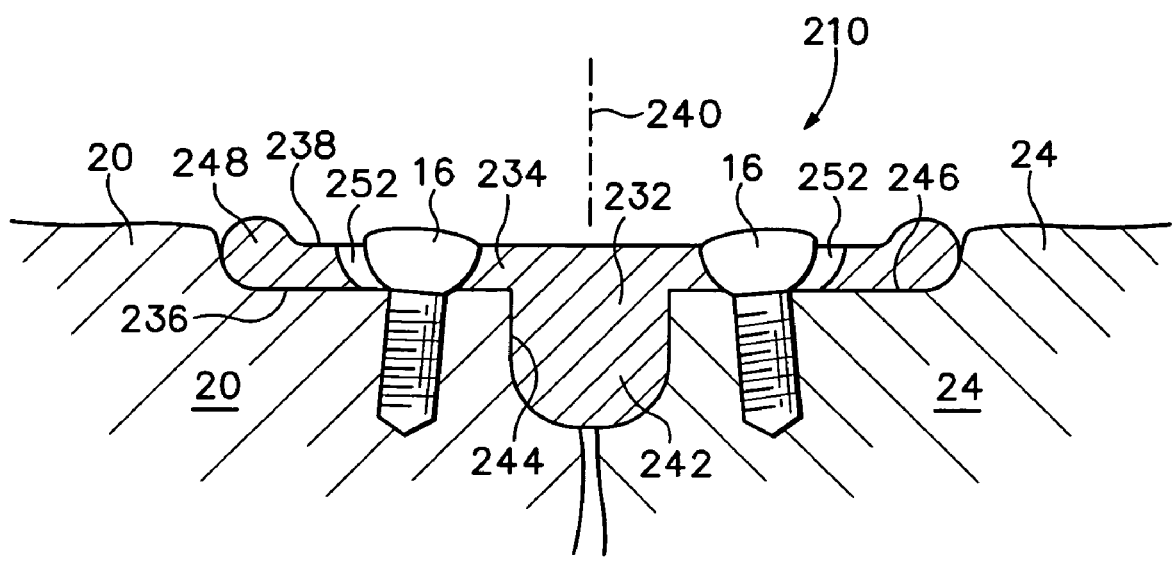
FIG. 9 is a sectional view of the bone plate of FIG. 8, viewed generally along line 9—9 of FIG. 8, after attachment to a plurality of carpal bones of the left hand using bone screws, in accordance with aspects of the invention.

FIGS. 8 and 9 show plan and sectional views, respectively, of another bone plate 210 for fusing two or more bones. In FIG. 9, plate 210 is attached to carpal bones 20, 24. Plate 210 may include a body portion 230 having a central region 232 and a lateral region 234 surrounding the central region. Each region may include a bone-facing surface 236 and a bone-opposing surface 238. The bone-facing surface may be generally planar.

Central region 232 may have any suitable position, size, shape, and relationship to the lateral region. The central region may intersect a central axis 240 defined by body portion 230 and may be partially or completely surrounded by lateral region 234. The bone-opposing surface of the central region may be generally co-planar with the bone-opposing surface of the lateral region, as shown here, or may be concave, to form a central depression or hole in the bone-opposing surface, among others. The central region may define a convex projection 242 extending from the bone-facing surface of the lateral region. The projection may be a post that is received in a hole 244 formed in bone, and may have any suitable structure, such as those described above for post portion 32 and post 50 or 150. Accordingly, projection 242 may have a positioning and/or centering function when plate 210 is applied to bone. The central region may include an aperture or may be free of apertures. In addition, the central region may be formed unitarily with the lateral region or may be a separate component. When the central region is a separate component, this region may be attached during manufacture, or removably by a user of the plate, for example, as described above for post portion 32.

Lateral region 234 also may have any suitable structure. The lateral region may define an annular structure that extends around central region 232. The lateral region may be generally planar, thus defining generally planar bone-facing and bone-opposing surfaces. Accordingly, the lateral region may be received by a generally planar recess 246 formed in the bones to be fused. Alternatively, the lateral region may be applied to the external bone surface without forming a corresponding recess in the bone. In either case, lateral region 234 may include a rounded lip or thickened perimeter 248. The rounded lip may function to minimize soft tissue irritation and thus the lip may be thickened relative to more centrally disposed sections of the lateral region, to increase the radius of curvature of the lip.

Lateral region 234 may define a plurality of openings for receiving bone screws 16. Each opening may be circular, such as opening 250, or configured to receive one screw at a discrete position. Such circular openings may include a counterbore 251. Alternatively, one more of the openings may be elongate to define slots 252. Slots 252 may extend radially from central axis 240. In addition, slots 252 may be compression slots having tapered counterbores 254. Each counterbore may taper along any suitable segment of the slot's long axis. Accordingly, a bone screw placed into bone at a more perimetrical or outer position of the counterbore may apply a radial force on the bone, towards the central axis, as the screw is tightened. As a result, the bone may slide centrally along the counterbore relative to the plate, helping to draw the bones together for fusion.

Bone plate 210 may be used to join a plurality of bones as follows. First, a reamer may be used to define central hole 244 and a surrounding recess 246 at a junction of two or more, and more typically, three or more bones. After plate 210 is positioned in the recess with post 242 in hole 244, a bone screw may be inserted into bone from circular opening 250, to provide a fixed relationship between the plate and one of the bones. Then bone screws may be inserted into the other bones through an appropriate subset or all of the slots. The other bones are pulled together and toward the one bone to which the plate is fixed as the bone screws are tightened in the slots against their respective counterbores.

The features described above may be suitable for use with other bone plates. More specifically, a projection, a cap, a rough texture on the bone-facing surface, one or more openings having plural discrete sites, and/or a thickened perimeter may be included on bone plates that have planar or concave bone-facing surfaces. For example, any suitable combination of these features may be included in elongate bone plates that fix long bones.

II.B. Example 2

This example describes selected aspects and embodiments of the invention, as a series of ordered paragraphs.

1. A bone plate for fusing at least two bones of a hand or foot, comprising: (A) a body portion having a convex, at least substantially hemispherical bone-facing surface; and (B) at least two openings defined by the body portion, the openings being configured to receive bone screws that attach the plate to each of the at least two bones and pull the bones together.

2. The bone plate of any one of the preceding or following paragraphs of this example, the body portion defining at least three openings, wherein the openings are configured to receive bone screws that attach the plate to each of at least three bones and pull the bones together.

3. The bone plate of any one of the preceding or following paragraphs of this example, wherein the bone-facing surface corresponds to less than half of a sphere.

4. The bone plate of any one of the preceding or following paragraphs of this example, wherein the bone-facing surface corresponds at least substantially to a spherical cap.

5. The bone plate of any one of the preceding or following paragraphs of this example, wherein the bone plate is formed of a biocompatible material.

6. The bone plate of any one of the preceding or following paragraphs of this example, the body portion defining a central axis, the openings being oriented so that the bones are compressed generally toward the central axis when the bone screws attach the plate to the bones.

7. The bone plate of any one of the preceding or following paragraphs of this example, the body portion defining a central axis, further comprising a projection that extends from the bone-facing surface parallel to the central axis.

8. The bone plate of any one of the preceding or following paragraphs of this example, wherein the body portion includes a central region and a projection disposed at the central region and projecting from the bone-facing surface.

9. The bone plate of paragraph 8, wherein projection is a post configured to be removable from the body portion.

10. The bone plate of any one of the preceding or following paragraphs of this example, wherein at least one of the openings is a slot.

11. The bone plate of any one of the preceding or following paragraphs of this example, wherein the bones are carpal bones of the hand.

12. A method of fusing at least two bones, comprising: (A) selecting a bone plate according any of the preceding or following paragraphs of this example; (B) forming a recess in the at least two bones capable of receiving the bone plate; (C) positioning the bone plate in the recess, such that the bone-facing surface of the bone plate adjoins the at least two bones; and (D) joining the bone plate to the at least two bones using bone screws.

13. A bone plate for fusing at least two bones of a hand or foot, the at least two bones defining a recess and a hole that extends into bone from the recess, the bone plate comprising: (A) a body portion configured to be received at least substantially in the recess, the body portion including a central region and an outer region at least partially surrounding the central region, the outer region including a convex bone-facing surface; (B) at least two openings disposed in the outer region of the body portion, the openings being configured to receive bone screws that attach the bone plate to the at least two bones; and (C) a projection extending from the central region of the body portion, beyond the bone-facing surface, the projection being configured to be received in the hole, thereby restricting movement of the body portion.

14. The bone plate of any one of the preceding or following paragraphs of this example, wherein the openings further are configured such that the bone screws pull the bones generally toward the central region.

15. The bone plate of any one of the preceding or following paragraphs of this example that refers to a projection, wherein the projection is configured to restrict movement of the body portion tangential to the bone-facing surface of the outer region.

16. The bone plate of any one of the preceding or following paragraphs of this example that refers to a projection, the body portion and the projection each defining a central axis, wherein the central axes are at least substantially aligned.

17. The bone plate of any one of the preceding or following paragraphs of this example, the body portion defining a central axis, wherein the openings are configured to direct the bone screws obliquely to the central axis.

18. The bone plate of any one of the preceding or following paragraphs of this example that refers to an outer region, wherein the bone-facing surface of the outer region is one of at least substantially hemispherical and at least substantially conical.

19. The bone plate of any one of the preceding or following paragraphs of this example that refers to a projection, wherein the projection comprises a separate component that is removable from the body portion.

20. The bone plate of any one of the preceding or following paragraphs of this example that refers to a projection and a central region, the central region of the body portion defining an aperture, wherein the projection is configured to be attached to the body portion at the aperture.

21. The bone plate of any one of the preceding or following paragraphs of this example that refers to a projection, wherein the projection and the body portion are configured for threadable engagement.

22. The bone plate of any one of the preceding or following paragraphs of this example that refers to a projection, wherein the projection is formed unitarily with the body portion.

23. The bone plate of any one of the preceding or following paragraphs of this example, further comprising a cap configured to be coupled to at least one of the body portion and the projection, the cap being configured to obstruct out-of-bone movement of at least one of the bone screws after the at least one bone screw has attached the body portion to one or more of the at least two bones.

24. The bone plate of any one of the preceding or following paragraphs of this example, the body portion defining at least three openings, wherein the openings are configured to receive bone screws that attach the plate to each of at least three bones and pull the bones together.

25. The bone plate of any one of the preceding or following paragraphs of this example, the body portion further including a perimeter and a bone-opposing surface that opposes the bone-facing surface, wherein the thickness of the perimeter is greater than the average thickness of the body portion measured between the bone-facing and bone-opposing surfaces.

26. A method of fusing bones, comprising: (A) selecting a bone plate according to any one of the preceding or following paragraphs of this example that refers to a projection and bone screws; (B) forming a recess in at least one of the at least two bones capable of receiving the body portion of the bone plate; (C) forming a hole in at least one of the at least two bones capable of receiving the projection of the bone plate; (D) positioning the bone plate in the recess and the hole, such that the bone-facing surface of the body portion and the projection both adjoin the at least two bones; and (E) joining the bone plate to the at least two bones using bone screws.

27. A bone plate for fusing at least two bones of a hand or foot, comprising:

(A) a body portion defining a central axis and having a convex bone-facing surface; and (B) at least two openings defined by the body portion, the openings being configured to receive bone screws that attach the plate to each of the at least two bones and pull the bones together generally toward the central axis, at least one of the openings being a slot.

28. The bone plate of any one of the preceding or following paragraphs of this example that refers to a slot, wherein the slot is arcuate when viewed generally normal to the slot.

29. The bone plate of any one of the preceding or following paragraphs of this example that refers to a slot and a central axis, the body portion having a perimeter, wherein the slot extends partially around the central axis and generally parallel to the perimeter.

30. The bone plate of paragraph 29, wherein the slot extends toward the central axis.

31. The bone plate of paragraph 30, wherein the slot is a compression slot with a tapered counterbore.

32. The bone plate of any one of the preceding or following paragraphs of this example, there being at least three openings defined by the body portion, wherein at least of the openings is at least substantially circular, and at least another two of the openings are slots.

33. The bone plate of paragraph 32, the at least two bones being at least three bones, wherein the at least three openings are disposed so that the plate can be fastened first to one of the bones using the circular opening, and next to at least two other bones at variable positions using the slots.

34. The bone plate of any one of the preceding or following paragraphs of this example that refers to a slot, the body portion defining an edge of the slot, wherein the edge is scalloped to form plural discrete sites, each of the discrete sites being configured to receive one bone screw.

35. The bone plate of paragraph 34, wherein the edge defines a counterbore for each of the discrete sites.

36. The bone plate of paragraph 35, wherein at least two of the plural discrete sites are spaced closely enough to prevent two bone screws from being fully inserted simultaneously into a bone at the at least two discrete sites.

37. The bone plate of any one of the preceding or following paragraphs of this example that refers to a slot, wherein the slot is configured to fully receive at least two bone screws.

38. The bone plate of any one of the preceding or following paragraphs of this example, wherein the body portion also defines at least one aperture for receiving a wire, the diameter of the at least one aperture for receiving the wire being substantially less than the diameter of each opening for receiving bone screws.

39. The bone plate of any one of the preceding or following paragraphs of this example, the body portion defining at least three openings, wherein the openings are configured to receive bone screws that attach the plate to each of at least three bones and pull the bones together generally toward the central axis.

40. The bone plate of any one of the preceding or following paragraphs of this example, further comprising a cap configured to be coupled to at least one portion of the bone plate, the cap being configured to obstruct out-of-bone movement of at least one bone screw after the at least one bone screw has attached the body portion to one or more bones.

41. The bone plate of any one of the preceding or following paragraphs of this example, wherein at least a portion of the bone-facing surface has a rough texture.

42. A method of fusing at least two bones, comprising: (A) selecting a bone plate according to any one of the preceding or following paragraphs of this example; (B) forming a recess in the at least two bones capable of receiving the bone plate; (C) positioning the bone plate in the recess, such that the bone-facing surface of the bone plate adjoins bone; and (D) joining the bone plate to the at least two bones using bone screws.

43. The method of paragraph 42, wherein the step of joining includes affixing the plate to a bone using a bone screw positioned through a circular opening, and then affixing the plate to another of the at least two bones using a bone screw positioned through a slot.

44. A bone plate for fusing at least two bones of a hand or foot, comprising:

(A) a body portion having a central region and a lateral region disposed around the central region, the central region including a convex bone-facing surface, the lateral region being generally planar; and (B) at least two openings defined by the lateral region, the two openings being slots, each slot extending toward the central region.

45. The bone plate of paragraph 44, the central region including a projection that projects from the bone-facing surface.

46. The bone plate of paragraph 44 or 45, the lateral region being annular.

47. The bone plate of any one of paragraphs 44–46, the lateral region defining at least one more opening that is circular.

48. The bone plate of any one of the preceding or following paragraphs that refers to slots, the slots being compression slots with tapered counterbores.

49. A bone plate for fusing plural bones, the plural bones defining a recess and a hole that extends into bone from the recess, the bone plate comprising: (A) a body portion configured to be received in the recess, the body portion including a bone-facing surface and a bone-opposing surface that opposes the bone-facing surface, the bone-facing surface being convex and configured to adjoin at least one of the plural bones in the recess, and the body portion defining plural openings and having a central region, the plural openings extending between the bone-facing and bone-opposing surfaces and being disposed lateral to the central region, the plural openings being configured to receive bone fasteners that attach the body portion to the plural bones and that radially compress the plural bones; and (B) a projection configured to be received in the hole, wherein the projection is joined to the body portion at the central region and extends beyond the bone-facing surface, and wherein the projection has a projection surface, the projection surface being configured to adjoin one or more of the plural bones when the body portion adjoins the at least one bone, so that movement of the body portion relative to the plural bones is restricted.

50. The bone plate of any one of the preceding or following paragraphs that refers to a projection, the projection having side walls, the side walls being at least substantially cylindrical.

51. The bone plate of any one of the preceding or following paragraphs that refers to a projection, the body portion and the projection being separate components.

52. The bone plate of any one of the preceding or following paragraphs that refers to a projection and a central region, the central region of the body portion defining an opening, the projection being configured to be received in the opening to join the projection to the body portion.

53. A bone plate for fusing plural bones that define a recess, comprising: (A) a body portion configured to be received in the recess, wherein the body portion includes a bone-facing surface and a bone-opposing surface that opposes the bone-facing surface, the bone-facing surface being convex and being configured to adjoin at least one of the plural bones in the recess, and wherein the body portion defines plural openings, the plural openings extending between the bone-facing and bone-opposing surfaces, the plural openings being configured to receive bone fasteners or bone screws that attach the body portion to the plural bones; and (B) a cap configured to be coupled to the body portion and configured to obstruct out-of-bone movement of at least one of the bone fasteners after the at least one bone fastener has attached the body portion to at least one of the plural bones.

54. The bone plate of any one of the preceding or following paragraphs, wherein the openings are configured to receive bone fasteners that compress the bones radially.

55. The bone plate of any one of the preceding or following paragraphs that refers to a cap, wherein the cap is configured to be threadably engaged with the body portion.

56. The bone plate of any one of the preceding or following paragraphs that refers to a cap, wherein the cap has a blocking portion configured to contact a head portion of at least one bone fastener before the at least one bone fastener moves completely out of bone.

57. The bone plate of any one of the preceding or following paragraphs that refers to a cap, the cap having a threaded portion joined to the blocking portion, wherein the threaded portion is configured to couple the cap to the body portion, the blocking portion and threaded portion each having a diameter, the diameter of the blocking portion being greater than the diameter of the threaded portion.

58. The bone plate of any one of the preceding or following paragraphs that refers to a cap, the body portion having a central region, the central region defining a hole, wherein the cap is configured to be received in the hole from the bone-opposing surface to couple the cap to the body portion.

59. The bone plate of any one of the preceding or following paragraphs that refers to a cap, the cap being configured to obstruct out-of-bone movement for each of the bone fasteners or bone fasteners that connects the bone plate to the bones.

60. A method of fusing at least two bones, comprising: (A) selecting a bone plate according to any one of the preceding or following paragraphs of this example that refers to a cap; (B) forming a recess in the at least two bones capable of receiving the bone plate; (C) positioning the bone plate in the recess, such that the bone-facing surface of the bone plate adjoins the at least two bones; (D) joining the bone plate to the at least two bones using bone screws; and (E) affixing the cap to the bone plate, such that out-of-bone movement of at least one of the bone screws is obstructed.

61. A bone plate for fusing plural bones that define a recess, comprising a body portion configured to be received in the recess, the body portion including a bone-facing surface and a bone-opposing surface that opposes the bone-facing surface, the bone-facing surface being convex and configured to adjoin the plural bones in the recess, and the body portion defining plural openings, the plural openings extending between the bone-facing and bone-opposing surfaces, the plural openings being configured to receive bone fasteners that attach the body portion to the plural bones and that radially compress the plural bones, wherein at least one of the plural openings includes plural discrete sites, each of the plural sites being configured to receive one bone fastener.

62. The bone plate of paragraph 61, each of the discrete sites being configured to position a nonoverlapping region of the body portion in contact with one of the bone fasteners.

63. The bone plate of paragraph 61 or 62, the body portion having an edge that defines the at least one opening, the edge also defining the plural discrete sites.

64. The bone plate of paragraph 63, the edge defining stop structures that separate the plural discrete sites, the stop structures being configured to allow the one fastener to move between the discrete sites when one bone fastener extends through the at least one opening with a shaft portion of the one fastener apposed to the edge, but to restrict the fastener to one of the discrete sites when the one fastener extends through the at least one opening with a head portion of the fastener contacting the edge.

65. The bone plate of any one of paragraphs 61–64, at least one opening being narrowed between the discrete sites.

66. The bone plate of any one of paragraphs 61–65, the plate having an edge that defines the at least one opening, the edge also defining a counterbore for each of the discrete sites.

67. The bone plate of any one of paragraphs 61–66, the plate having a central region, the plural openings being disposed lateral to the central region, the plural openings including at least one aperture configured to receive only one of the bone fasteners so that the bone fastener prohibits rotation of the plate about the central axis.

68. The bone plate of any one of paragraphs 61–67, at least two of the plural discrete sites being spaced closely enough to prevent fully inserting two of the bone fasteners into bone at the at least two discrete sites.

69. The bone plate of any one of paragraphs 61–68, the at least one opening being configured to receive at least two of the bone fasteners with the at least two bone fasteners fully inserted into bone.

70. A bone plate for fusing plural bones that define a recess, comprising a body portion configured to be received in the recess, the body portion including a bone-facing surface and a bone-opposing surface that opposes the bone-facing surface, the bone-facing surface being convex and configured to contact at least one of the plural bones in the recess, and the body portion defining plural openings, the plural openings extending between the bone-facing and bone-opposing surfaces, the plural openings being configured to receive bone fasteners that attach the body portion to the plural bones and that radially compress the plural bones, wherein the bone-facing surface includes a region configured to have a rough texture.

71. The bone plate of paragraph 70, the bone-opposing surface having an average texture, the region having the rough texture being palpably rougher than the average texture.

72. The bone plate of paragraph 70 or 71, the bone-facing surface having an area, the region having the rough texture occupying at least half of the area.

73. A bone plate for fusing plural bones that define a recess, comprising a body portion configured to be received in the recess, the body portion including a bone-facing surface and a bone-opposing surface that opposes the bone-facing surface, the bone-facing surface being convex and configured to contact at least one of the plural bones in the recess, the body portion defining plural openings, the plural openings extending between the bone-facing and bone-opposing surfaces, the plural openings being configured to receive bone fasteners that attach the body portion to the plural bones and that radially compress the plural bones, wherein the body portion includes a perimeter and an average thickness measured between the bone-facing and bone-opposing surface, the perimeter having a thickness that is greater than the average thickness.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method of fusing at least two bones of a hand or a foot, comprising:
    selecting a bone plate including a body portion with a bone-facing surface and further including a post extending from the bone-facing surface of the body portion;
    forming a cavity defined by at least two bones of a hadn or a foot, the step of forming including a step of reaming to form a portion of the cavity;
    placing the bone plate into the cavity such that the body portion is received in the portion of the cavity and such that the post restricts movement of the body portion; and
    attaching the bone plate to the at least two bones using fasteners,
    wherein the step of reaming forms adjoining first and second portions of the cavity, wherein the first portion of the cavity is shaped according to the bone-facing surface, and wherein the second portion of the cavity is shaped according to the post,
    wherein the steps of placing disposes the post in the second portion of the cavity, and wherein the second portion of the cavity is formed partially by a pre-existing gap between the at least two bones.

2. The method of claim 1, wherein the first and second portions of the cavity are formed in a single step.

3. The method of claim 1, wherein the step of selecting includes a step of selecting a bone plate including a bone-facing surface that is convex, and wherein the step of forming includes a step of forming a cavity at least partially defined by a concave bone surface.

4. The method of claim 1, wherein the step of selecting includes a step of selecting a bone plate including a post formed unitarily with the body portion.

5. The method of claim 1, wherein the step of selecting includes a step of selecting a bone plate including a post that is a separate component attached to the body portion, and wherein the step of placing includes a step of placing the body portion and the post as a unit into the cavity.

6. The method of claim 1, wherein the step of selecting includes a step of selecting a bone plate having a post disposed in threaded engagement with the body portion.

7. The method of claim 1, wherein the step of selecting includes a step of selecting a bone plate including a post substantially centered on the body portion.

8. The method of claim 1, wherein the step of selecting includes a step of selecting a bone plate including a body portion with a bone-facing surface having a rough texture, and wherein the step of placing positions the rough texture adjacent bone.

9. The method of claim 1, wherein the step of selecting includes a step of selecting a bone plate including a body portion with a bone-facing surface corresponding to a portion of a sphere.

10. The method of claim 1, wherein the step of selecting includes a step of selecting a bone plate including a body portion having a bone-opposing surface and a central region, and wherein the central region defines a blind opening extending into the body portion from the bone-opposing surface.

11. The method of claim 1, wherein the step of selecting includes a step of selecting a bone plate defining a central axis and a plurality of openings arranged around the central axis, wherein each of the plurality of openings defines an axis extending obliquely to the central axis, and wherein the step of attaching includes a step of placing bone screws through at least two of the plurality of openings.

12. The method of claim 1, wherein the step of selecting includes a step of selecting a bone plate including a cap configured to be attached to the body portion such that the cap obstructs out-of-bone movement of at least one of the fasteners after the at least one fastener has attached the body portion to bone.

13. The method of claim 1, wherein the step of selecting includes a step of selecting a body portion defining at least one slot configured such that a bone screw can be placed at multiple positions along the slot.

14. The method of claim 1, wherein the body portion further includes a perimeter and a bone-opposing surface that opposes the bone-facing surface, and wherein the thickness of the perimeter is greater than the average thickness of the body portion measured between the bone-facing and bone-opposing surfaces.

15. The method of claim 1, wherein the bone-facing surface corresponds to a portion of a sphere having a center, and wherein the step of placing restricts pivotal motion of the body portion about a plurality of axes extending through the center.

16. The method of claim 1, the bone plate including a plurality of openings, wherein the step of attaching including a step of placing bone screws through the plurality of openings and into the at least two bones.

17. The method of claim 1, wherein the step of selecting includes a step of selecting a body portion having a width and a height, and wherein the height is substantially less than half the width.

18. The method of claim 1, wherein the step of selecting includes a step of selecting a body portion and a post each having a width, and wherein the width of the post is about one-fifth the width of the body portion.

19. The method of claim 1, wherein the step of selecting includes a step of selecting a bone plate with a body portion having a height measured parallel to a central axis defined by the post, and wherein the post extends from the bone-facing surface by a distance less than the height.

20. A method of fusing at least two bones, comprising:
    selecting a bone plate including a body portion with a bone-facing surface and further including a post connected to the body portion and extending from the bone-facing surface of the body portion;
    placing the bone plate into a cavity formed by at least two bones of a hand or a foot such that the post restricts movement of the body portion; and
    attaching the bone plate to the at least two bones using fasteners,
    wherein placing the bone plate into a cavity is performed while the post remains connected to the body portion, wherein the body portion further includes a perimeter and a bone-opposing surface that opposes the bone-facing surface, and wherein the thickness of the perimeter is greater than the average thickness of the body portion measured between the bone-facing and bone-opposing surfaces.

21. The method of claim 20, further comprising a step of forming adjoining first and second portions of the cavity, wherein the first portion of the cavity is shaped according to the bone-facing surface, and wherein the second portion of the cavity is shaped according to the post.

22. The method of claim 21, wherein the first and second portions of the cavity are formed in a single step.

23. The method of claim 21, wherein the step of selecting includes a step of selecting a bone plate including a bone-facing surface that is convex, and wherein the step of forming includes a step of forming a cavity at least partially defined by a concave bone surface.

24. The method of claim 20, wherein the step of selecting includes a step of selecting a bone plate including a post formed unitarily with the body portion.

25. The method of claim 20, wherein the step of selecting includes a step of selecting a bone plate including a post that is a separate component attached to the body portion, and wherein the step of placing includes a step of placing the body portion and the post as a unit into the cavity.

26. The method of claim 20, wherein the step of selecting includes a step of selecting a bone plate having a post disposed in threaded engagement with the body portion.

27. The method of claim 20, wherein the step of selecting includes a step of selecting a bone plate including a post substantially centered on the body portion.

28. The method of claim 20, wherein the step of selecting includes a step of selecting a bone plate including a body portion with a bone-facing surface having a rough texture, and wherein the step of placing positions the rough texture adjacent bone.

29. The method of claim 20, wherein the step of selecting includes a step of selecting a bone plate including a body portion with a bone-facing surface corresponding to a portion of a sphere.

30. The method of claim 20, wherein the step of selecting includes a step of selecting a bone plate including a body portion having a bone-opposing surface and a central region, and wherein the central region defines a blind opening extending into the body portion from the bone-opposing surface.

31. The method of claim 20, wherein the step of selecting includes a step of selecting a bone plate defining a central axis and a plurality of openings arranged around the central axis, wherein each of the plurality of openings defines an axis extending obliquely to the central axis, and wherein the step of attaching includes a step of placing bone screws through at least two of the plurality of openings.

32. The method of claim 20, wherein the step of selecting includes a step of selecting a bone plate including a cap configured to be attached to the body portion such that the cap obstructs out-of-bone movement of at least one of the fasteners after the at least one fastener has attached the body portion to bone.

33. The method of claim 20, wherein the step of selecting includes a step of selecting a body portion defining at least one slot configured such that a bone screw can be placed at multiple positions along the slot.

34. The method of claim 20, wherein the bone-facing surface corresponds to a portion of a sphere having a center, and wherein the step of placing restricts pivotal motion of the body portion about a plurality of axes extending through the center.

35. The method of claim 20, the bone plate including a plurality of openings, wherein the step of attaching including a step of placing bone screws through the plurality of openings and into the at least two bones.

36. The method of claim 20, wherein the step of selecting includes a step of selecting a body portion having a width and a height, and wherein the height is substantially less than half the width.

37. The method of claim 20, wherein the step of selecting includes a step of selecting a body portion and a post each having a width, and wherein the width of the post is about one-fifth the width of the body portion.

38. The method of claim 20, wherein the step of selecting includes a step of selecting a bone plate with a body portion having a height measured parallel to a central axis defined by the post, and wherein the post extends from the bone-facing surface by a distance less than the height.

39. A method of fusing at least two bones of a hand, comprising:
selecting a bone plate including a body portion with a bone-facing surface and further including a post connected to the body portion and extending from the bone-facing surface of the body portion;
placing the bone plate into a cavity formed by at least two bones of a hand such that the post extends into a portion of the cavity defined by at least a pair of carpal bones of the hand to restrict movement of the body portion; and
attaching the bone plate to the at least two bones using fasteners,
wherein placing the bone plate into a cavity is performed while the post remains connected to the body portion.

40. The method of claim 39, further comprising a step of forming adjoining first and second portions of the cavity, wherein the first portion of the cavity is shaped according to the bone-facing surface, and wherein the second portion of the cavity is shaped according to the post.

41. The method of claim 40, wherein the first and second portions of the cavity are formed in a single step.

42. The method of claim 40, wherein the step of selecting includes a step of selecting a bone plate including a bone-facing surface that is convex, and wherein the step of forming includes a step of forming a cavity at least partially defined by a concave bone surface.

43. The method of claim 39, wherein the step of selecting includes a step of selecting a bone plate including a post formed unitarily with the body portion.

44. The method of claim 39, wherein the step of selecting includes a step of selecting a bone plate including a post that is a separate component attached to the body portion, and wherein the step of placing includes a step of placing the body portion and the post as a unit into the cavity.

45. The method of claim 39, wherein the step of selecting includes a step of selecting a bone plate having a post disposed in threaded engagement with the body portion.

46. The method of claim 39, wherein the step of selecting includes a step of selecting a bone plate including a post substantially centered on the body portion.

47. The method of claim 39, wherein the step of selecting includes a step of selecting a bone plate including a body portion with a bone-facing surface having a rough texture, and wherein the step of placing positions the rough texture adjacent bone.

48. The method of claim 39, wherein the step of selecting includes a step of selecting a bone plate including a body portion with a bone-facing surface corresponding to a portion of a sphere.

49. The method of claim 39, wherein the step of selecting includes a step of selecting a bone plate including a body portion having a bone-opposing surface and a central region, and wherein the central region defines a blind opening extending into the body portion from the bone-opposing surface.

50. The method of claim 39, wherein the step of selecting includes a step of selecting a bone plate defining a central axis and a plurality of openings arranged around the central axis, wherein each of the plurality of openings defines an axis extending obliquely to the central axis, and wherein the step of attaching includes a step of placing bone screws through at least two of the plurality of openings.

51. The method of claim 39, wherein the step of selecting includes a step of selecting a bone plate including a cap configured to be attached to the body portion such that the cap obstructs out-of-bone movement of at least one of the fasteners after the at least one fastener has attached the body portion to bone.

52. The method of claim 39, wherein the step of selecting includes a step of selecting a body portion defining at least one slot configured such that a bone screw can be placed at multiple positions along the slot.

53. The method of claim 39, wherein the body portion further includes a perimeter and a bone-opposing surface that opposes the bone-facing surface, and wherein the thickness of the perimeter is greater than the average thickness of the body portion measured between the bone-facing and bone-opposing surfaces.

54. The method of claim 39, wherein the bone-facing surface corresponds to a portion of a sphere having a center, and wherein the step of placing restricts pivotal motion of the body portion about a plurality of axes extending through the center.

55. The method of claim 39, the bone plate including a plurality of openings, wherein the step of attaching including a step of placing bone screws through the plurality of openings and into the at least two bones.

56. The method of claim 39, wherein the step of selecting includes a step of selecting a body portion having a width and a height, and wherein the height is substantially less than half the width.

57. The method of claim 39, wherein the step of selecting includes a step of selecting a body portion and a post each having a width, and wherein the width of the post is about one-fifth the width of the body portion.

58. The method of claim 39, wherein the step of selecting includes a step of selecting a bone plate with a body portion having a height measured parallel to a central axis defined by the post, and wherein the post extends from the bone-facing surface by a distance less than the height.

59. A method of fusing at least two bones of a hand, comprising:
  selecting a bone plate including a body portion with a bone-facing surface and further including a post connected to the body portion and extending from the bone-facing surface of the body portion;
  placing the bone plate into a cavity formed by at least two bones of a hand such that the post restricts movement of the body portion and such that the body portion is disposed in a recess formed selectively on a dorsal side of the at least two bones; and
  attaching the bone plate to the at least two bones using fasteners,
  wherein placing the bone plate into a cavity is performed while the post remains connected to the body portion.

60. The method of claim 59, further comprising a step of forming adjoining first and second portions of the cavity, wherein the first portion of the cavity is shaped according to the bone-facing surface, and wherein the second portion of the cavity is shaped according to the post.

61. The method of claim 60, wherein the first and second portions of the cavity are formed in a single step.

62. The method of claim 60, wherein the step of selecting includes a step of selecting a bone plate including a bone-facing surface that is convex, and wherein the step of forming includes a step of forming a cavity at least partially defined by a concave bone surface.

63. The method of claim 59, wherein the step of selecting includes a step of selecting a bone plate including a post formed unitarily with the body portion.

64. The method of claim 59, wherein the step of selecting includes a step of selecting a bone plate including a post that is a separate component attached to the body portion, and wherein the step of placing includes a step of placing the body portion and the post as a unit into the cavity.

65. The method of claim 59, wherein the step of selecting includes a step of selecting a bone plate having a post disposed in threaded engagement with the body portion.

66. The method of claim 59, wherein the step of selecting includes a step of selecting a bone plate including a post substantially centered on the body portion.

67. The method of claim 59, wherein the step of selecting includes a step of selecting a bone plate including a body portion with a bone-facing surface having a rough texture, and wherein the step of placing positions the rough texture adjacent bone.

68. The method of claim 59, wherein the step of selecting includes a step of selecting a bone plate including a body portion with a bone-facing surface corresponding to a portion of a sphere.

69. The method of claim 59, wherein the step of selecting includes a step of selecting a bone plate including a body portion having a bone-opposing surface and a central region, and wherein the central region defines a blind opening extending into the body portion from the bone-opposing surface.

70. The method of claim 59, wherein the step of selecting includes a step of selecting a bone plate defining a central axis and a plurality of openings arranged around the central axis, wherein each of the plurality of openings defines an axis extending obliquely to the central axis, and wherein the step of attaching includes a step of placing bone screws through at least two of the plurality of openings.

71. The method of claim 59, wherein the step of selecting includes a step of selecting a bone plate including a cap configured to be attached to the body portion such that the cap obstructs out-of-bone movement of at least one of the fasteners after the at least one fastener has attached the body portion to bone.

72. The method of claim 59, wherein the step of selecting includes a step of selecting a body portion defining at least one slot configured such that a bone screw can be placed at multiple positions along the slot.

73. The method of claim 59, wherein the body portion further includes a perimeter and a bone-opposing surface that opposes the bone-facing surface, and wherein the thickness of the perimeter is greater than the average thickness of the body portion measured between the bone-facing and bone-opposing surfaces.

74. The method of claim 59, wherein the bone-facing surface corresponds to a portion of a sphere having a center, and wherein the step of placing restricts pivotal motion of the body portion about a plurality of axes extending through the center.

75. The method of claim 59, the bone plate including a plurality of openings, wherein the step of attaching including a step of placing bone screws through the plurality of openings and into the at least two bones.

76. The method of claim 59, wherein the step of selecting includes a step of selecting a body portion having a width and a height, and wherein the height is substantially less than half the width.

77. The method of claim 59, wherein the step of selecting includes a step of selecting a body portion and a post each having a width, and wherein the width of the post is about one-fifth the width of the body portion.

78. The method of claim 59, wherein the step of selecting includes a step of selecting a bone plate with a body portion having a height measured parallel to a central axis defined by the post, and wherein the post extends from the bone-facing surface by a distance less than the height.

* * * * *